(12) United States Patent
Behdad et al.

(10) Patent No.: US 10,765,477 B2
(45) Date of Patent: Sep. 8, 2020

(54) MICROWAVE ABLATION ANTENNA SYSTEM

(71) Applicant: Wisconsin Alumni Research Foundation, Madison, WI (US)

(72) Inventors: Nader Behdad, Madison, WI (US);
Susan C. Hagness, Madison, WI (US);
Hung Thanh Luyen, Madison, WI (US)

(73) Assignee: Wisconsin Alumni Research Foundation, Madison, WI (US)

(*) Notice: Subject to any disclaimer, the term of this patent is extended or adjusted under 35 U.S.C. 154(b) by 98 days.

(21) Appl. No.: 14/202,786

(22) Filed: Mar. 10, 2014

(65) Prior Publication Data

US 2015/0250540 A1    Sep. 10, 2015

(51) Int. Cl.
*A61B 18/18* (2006.01)
*H01Q 9/42* (2006.01)
*A61B 18/00* (2006.01)

(52) U.S. Cl.
CPC ............ *A61B 18/1815* (2013.01); *H01Q 9/42* (2013.01); *A61B 2018/00529* (2013.01); *A61B 2018/00577* (2013.01); *A61B 2018/1846* (2013.01); *A61B 2018/1853* (2013.01); *A61B 2018/1892* (2013.01)

(58) Field of Classification Search
CPC .......... A61B 18/1815; A61B 2018/183; A61B 2018/1823; A61B 2018/1853; A61B 2018/1876
See application file for complete search history.

(56) References Cited

U.S. PATENT DOCUMENTS 5,246,438 A * 9/1993 Langberg ............... A61B 18/08
600/374
5,300,099 A 4/1994 Rudie
(Continued)

FOREIGN PATENT DOCUMENTS

JP  2004-311334  11/2004
JP  2008-142467  6/2008

OTHER PUBLICATIONS

J Reinholm, The Characteristic Impedance of Coaxial Cables. Jun. 14, 2012. Electronics-lab.com, accessed Sep. 18, 2015. http://www.electronics-lab.com/the-characteristic-impedance-of-coaxial-cables/.*

(Continued)

*Primary Examiner* — Linda C Dvorak
*Assistant Examiner* — Bo Ouyang
(74) *Attorney, Agent, or Firm* — Bell & Manning, LLC

(57) ABSTRACT

An antenna system is provided. The antenna system includes a coaxial cable, an antenna, and an impedance matching structure. The coaxial cable includes a center conductor extending a length of the coaxial cable, a dielectric material surrounding the center conductor along the length of the coaxial cable, and a conductive shield surrounding the dielectric material along the length of the coaxial cable. The antenna includes a conductor having an electrical length of half a wavelength at a selected operating frequency. The impedance matching structure includes a second center conductor mounted between an end of the center conductor of the coaxial cable and a feed end of the antenna. The impedance matching structure is configured to match an impedance of the coaxial cable to an impedance of the antenna.

20 Claims, 16 Drawing Sheets

(56) References Cited

U.S. PATENT DOCUMENTS

| | | | |
|---|---|---|---|
| 5,683,382 A | 11/1997 | Lenihan | |
| 6,051,018 A | 4/2000 | Larsen | |
| 7,118,590 B1* | 10/2006 | Cronin | A61B 18/14 606/33 |
| 7,194,297 B2 | 3/2007 | Talpade et al. | |
| 7,226,446 B1 | 6/2007 | Mody et al. | |
| 7,826,904 B2* | 11/2010 | Appling | A61B 18/18 606/33 |
| 8,059,059 B2* | 11/2011 | Bonn | A61B 18/18 343/793 |
| 8,280,525 B2* | 10/2012 | Rusin | A61B 18/18 607/101 |
| 8,414,570 B2 | 4/2013 | Turner et al. | |
| 2006/0189973 A1 | 8/2006 | van der Weide | |
| 2009/0076492 A1* | 3/2009 | Behnke | A61B 18/18 606/33 |
| 2010/0057070 A1* | 3/2010 | Behnke | A61B 18/18 606/33 |
| 2010/0097284 A1 | 4/2010 | Brannan et al. | |
| 2010/0125269 A1 | 5/2010 | Emmons et al. | |
| 2010/0168727 A1* | 7/2010 | Hancock | A61B 18/18 606/33 |
| 2010/0185192 A1* | 7/2010 | Muller | A61B 18/18 606/33 |
| 2010/0217252 A1 | 8/2010 | Rossetto et al. | |
| 2010/0228244 A1* | 9/2010 | Hancock | A61B 18/1815 606/33 |
| 2010/0305561 A1 | 12/2010 | Prakash et al. | |
| 2011/0034917 A1* | 2/2011 | Brannan | A61B 18/00 606/41 |
| 2011/0208177 A1* | 8/2011 | Brannan | A61B 18/1815 606/33 |
| 2011/0238060 A1 | 9/2011 | Lee, Jr. et al. | |
| 2014/0358140 A1 | 1/2014 | Emmons | |

OTHER PUBLICATIONS

International Search Report and Written Opinion for Intl. Patent Appl. No. PCT/US2015/012615, dated May 1, 2015, 10 pp.
International Search Report and Written Opinion for PCT/US2018/067469, dated Apr. 18, 2019.

* cited by examiner

MICROWAVE ABLATION ANTENNA SYSTEM

REFERENCE TO GOVERNMENT RIGHTS

This invention was made with government support under N00014-11-1-0618 awarded by the NAVY/ONR. The government has certain rights in the invention.

BACKGROUND

Microwave ablation (MWA) is a form of thermal ablation used in interventional radiology to treat cancer. MWA uses electromagnetic waves in the microwave energy spectrum (300 megahertz to 300 gigahertz) to produce tissue-heating effects. MWA is generally used for minimally invasive treatment and/or palliation of solid tumors in patients. MWA offers several advantages over other ablation technologies such as radiofrequency (RF) and cryoablation including higher temperatures than RF, larger ablation zone volumes, shorter ablation times, and better ablation performance near arteries, which act as heat sinks.

Typically, interstitial antennas used for MWA are implemented using coaxial cables. When a balanced antenna is fed by an unbalanced transmission line unwanted electric currents are excited on the outer conductors of the feeding coaxial cables. If not properly suppressed, these currents can result in undesired heating and potentially ablation of healthy tissue along the insertion path of the antenna. Balanced to unbalanced transformers (Baluns) are generally implemented to solve this problem. A balun uses a hollow circular conductor to encompass the feeding coaxial cable and, depending on the design, may or may not be electrically connected to it.

SUMMARY

An antenna system is provided. The antenna system includes, but is not limited to, a coaxial cable, an antenna, and an impedance matching structure. The coaxial cable includes, but is not limited to, a center conductor extending a length of the coaxial cable, a dielectric material surrounding the center conductor along the length of the coaxial cable, and a conductive shield surrounding the dielectric material along the length of the coaxial cable. The antenna includes, but is not limited to, a conductor having an electrical length of half a wavelength at a selected operating frequency. The impedance matching structure includes, but is not limited to, a second center conductor mounted between an end of the center conductor of the coaxial cable and a feed end of the antenna. The impedance matching structure is configured to match an impedance of the coaxial cable to an impedance of the antenna.

A transmitter is provided that includes the antenna system, a signal generator, and a connector. The signal generator is configured to generate a signal at the selected operating frequency. The connector is configured to connect a second end of the coaxial cable opposite the end of the center conductor to the signal generator to receive the generated signal.

Other principal features of the disclosed subject matter will become apparent to those skilled in the art upon review of the following drawings, the detailed description, and the appended claims.

BRIEF DESCRIPTION OF THE DRAWINGS

Illustrative embodiments of the disclosed subject matter will hereafter be described referring to the accompanying drawings, wherein like numerals denote like elements.

DETAILED DESCRIPTION

Figure 1:
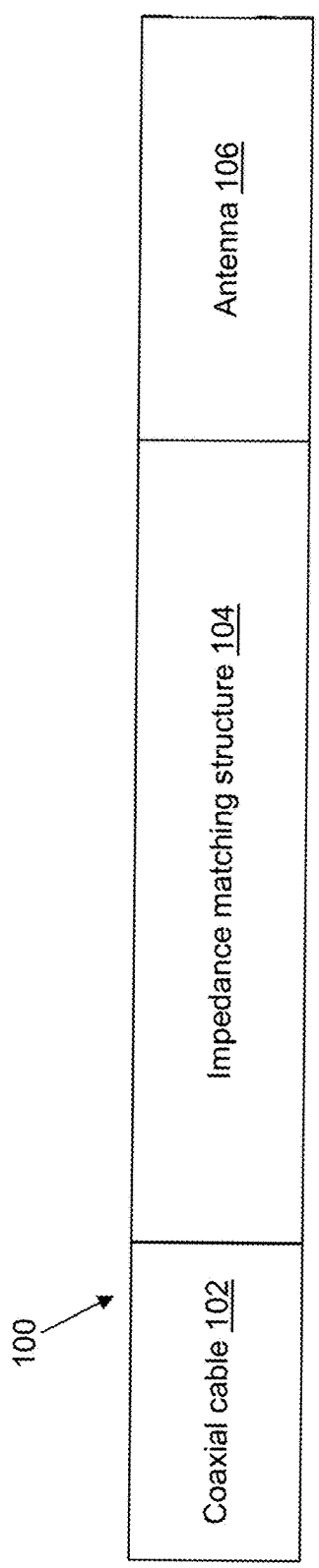
FIG. 1 depicts a block diagram of a microwave ablation (MWA) antenna system in accordance with an illustrative embodiment.

With reference to FIG. 1, a block diagram of an antenna system 100 is shown in accordance with an illustrative embodiment. Antenna system 100 may include a coaxial cable 102, an impedance matching structure 104, and an antenna 106. Impedance matching structure 104 is configured to match an impedance of coaxial cable 102 to an impedance of antenna 106. Antenna system 100 may be used to perform microwave ablation (MWA), for example, of tissue. Antenna 106 may be any base fed monopole type antenna such as a monopole antenna, a helical antenna, a whip antenna, a rubber ducky antenna, a random wire antenna, an umbrella antenna, an inverted-L antenna, a T-antenna, a mast radiator, a ground plane antenna, a bent wire antenna, etc. Coaxial cable 102 may include any length of coaxial cable having any characteristic impedance.

Figure 2:
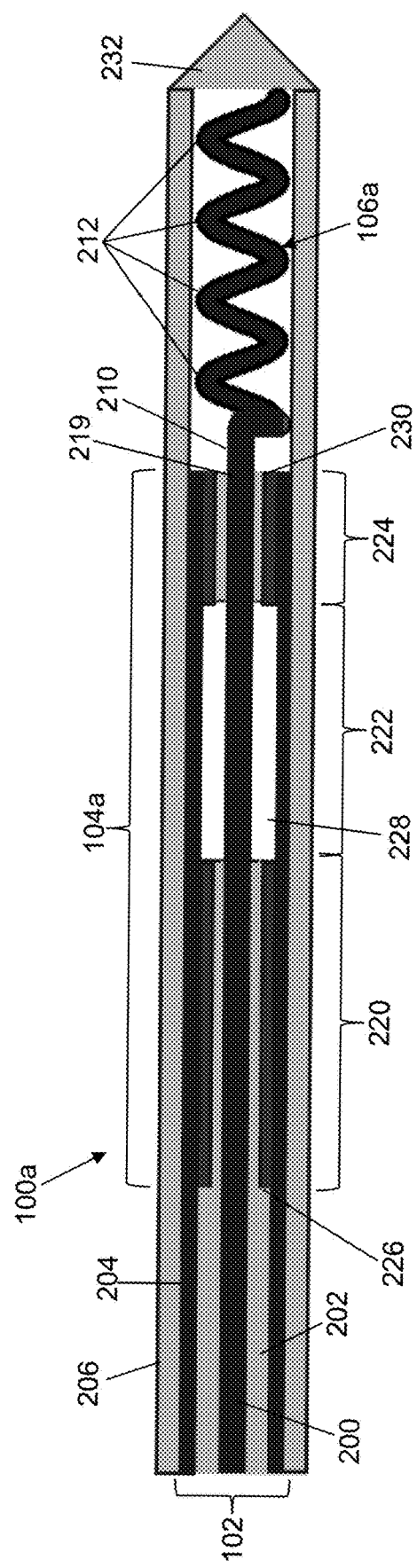
FIG. 2 depicts a side cross sectional view of an MWA antenna system of FIG. 1 in accordance with an illustrative embodiment.

With reference to FIG. 2, a side cross-sectional view of a first antenna system 100a is shown in accordance with an illustrative embodiment. First antenna system 100a may include coaxial cable 102, a first impedance matching structure 104a, and a first antenna 106a. First impedance matching structure 104a is configured to match the impedance of coaxial cable 102 to an impedance of first antenna 106a.

Coaxial cable 102 may include a center conductor 200 extending a length of coaxial cable 102, a dielectric material 202 surrounding center conductor 200 along the length of coaxial cable 102, a conductive shield 204 surrounding dielectric material 202 along the length of coaxial cable 102, and an insulating jacket 206 surrounding conductive shield 204 along the length of coaxial cable 102. Center conductor 200 is generally circular and may be formed of a solid conductive material such as copper plated steel wire, silver plated steel wire, silver plated copper wire, silver plated copper clad steel wire, copper wire, copper clad aluminum wire, steel wire, etc. Coaxial cable 102 may have a variety of diameters. Dielectric material 102 may include foamed polyethylene, solid polyethylene, polyethylene foam, polytetrafluoroethylene, air, air space polyethylene, vacuum, etc. Conductive shield 204 may be formed of a solid or braided conductive material such as copper, steel, aluminum, silver plated copper, silver plated copper clad steel, etc. Insulating jacket 206 can be made from many different insulating materials such as polyvinyl chloride or another plastic material.

Coaxial cable 102 may be rigid, semi-rigid, or flexible. The characteristic impedance may be off the shelf and range between approximately 20 and approximately 125 ohms or be designed to have a selected characteristic impedance within, above, or below this range as understood by a person of skill in the art using various dielectric and conductive materials, diameters, and thicknesses.

First antenna 106a is a helical antenna formed of a conducting wire wound in the form of a helix. The dimensions of the helix (diameter and pitch) are small compared with the wavelength so that first antenna 106a acts similar to a monopole antenna. First antenna 106a may include a feed connector 210 and a plurality of helical turns 212. First antenna 106a is formed of a conductive material. The plurality of helical turns 212 have an electrical length of half a wavelength at a selected operating frequenc, which is also known as a second resonance mode. As known to a person of skill in the art, the wavelength of operation, $\lambda_o$, of antenna system 100 is defined as $\lambda_o = c/f_o$, where c is the speed of light in an environment in which antenna system 100 is used, such as a body tissue, and $f_o$ is the selected operating frequency.

At a frequency where the electrical length of the plurality of helical turns 212 is approximately half a wavelength, an electric current at feed connector 210 achieves a minimum while the voltage is maximized. The resulting high input impedance creates a natural choke point for the currents that tend to flow on the outer surface of conductive shield 204 of coaxial cable 102 eliminating the need to use a balun. Despite the high feed-point impedance, matching between first antenna 106a and coaxial cable 102 can be achieved using first impedance matching structure 104a.

First impedance matching structure 104a is mounted between coaxial cable 102 and a feed end 219 of feed connector 210 of first antenna 106a. First impedance matching structure 104a may include a first capacitive section 220, an inductive section 222, and a second capacitive section 224. First impedance matching structure 104a may be formed from an extension of coaxial cable 102. First capacitive section 220, inductive section 222, and second capacitive section 224 may include center conductor 200 extending a length of first capacitive section 220, inductive section 222, and second capacitive section 224. Feed connector 210 is electrically connected to center conductor 200 extending from second capacitive section 224.

First capacitive section 220 further may include dielectric material 202 surrounding center conductor 200 along the length of first capacitive section 220, conductive shield 204 surrounding dielectric material 202 along the length of first capacitive section 220, and insulating jacket 206 surrounding conductive shield 204 along the length of first capacitive section 220. A portion of dielectric material 202 is removed along the length of first capacitive section 220 adjacent conductive shield 204. A second conductive material 226 is inserted to replace the removed portion of dielectric material 202. In an alternative embodiment, all of dielectric material 202 is removed along the length of first capacitive section 220 adjacent conductive shield 204, and conductive material 226 is inserted to replace a portion of the removed dielectric material 202 and a different, or the same, dielectric material is inserted to replace the remaining portion of the removed dielectric material 202. In an illustrative embodiment, second conductive material 226 is copper.

Dielectric material 202 surrounding center conductor 200 may be removed along the length of inductive section 222 and replaced with a second dielectric material 228 having a lower dielectric constant than dielectric material 202. In an illustrative embodiment, second dielectric material 228 is a gas such as air, oxygen, nitrogen, that has a dielectric constant close to that of vacuum, i.e., approximately one. Conductive shield 204 surrounds second dielectric material 228 along the length of inductive section 222 and insulating jacket 206 surrounds conductive shield 204 along the length of inductive section 222.

Second capacitive section 224 further may include dielectric material 202 surrounding center conductor 200 along the length of second capacitive section 224, conductive shield 204 surrounding dielectric material 202 along the length of second capacitive section 224, and insulating jacket 206 surrounding conductive shield 204 along the length of second capacitive section 224. A portion of dielectric material 202 is removed along the length of second capacitive section 224 adjacent conductive shield 204. A third conductive material 230 is inserted to replace the removed portion of dielectric material 202. In an alternative embodiment, all of dielectric material 202 is removed along the length of second capacitive section 224 adjacent conductive shield 204, and third conductive material 230 is inserted to replace a portion of the removed dielectric material 202 and a different, or the same, dielectric material is inserted to replace the remaining portion of the removed dielectric material 202. In an illustrative embodiment, third conductive material 230 is copper.

In an illustrative embodiment, insulating jacket 206 surrounds first antenna 106a. A cover 232 may extend across an end of insulating jacket 206 to enclose first antenna 106a. Insulating jacket 206 and cover 232 may be mounted to allow movement relative to first antenna 106a so that first antenna 106a is protected while antenna system 100a is inserted into a tissue and is exposed once inserted into the tissue.

Figure 3A:
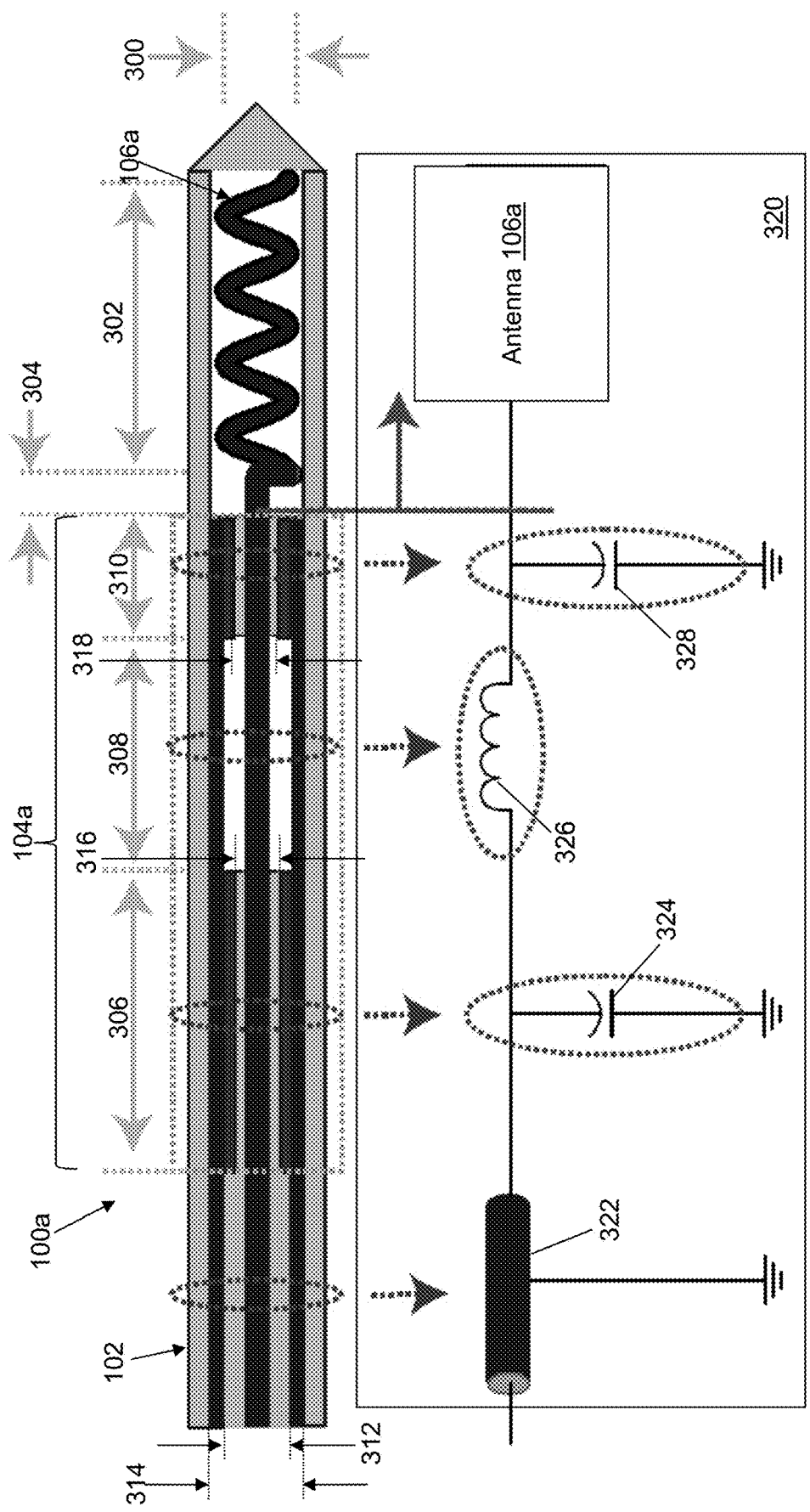
FIG. 3a depicts the view of the MWA antenna system of FIG. 2 and an equivalent circuit model of the MWA antenna system of FIG. 2 in accordance with an illustrative embodiment.

Referring to FIG. 3a, the plurality of helical turns 212 of first antenna 106a have a diameter 300, a total height 302, and a number of turns, n. Diameter 300, total height 302, and n can be determined, for example, using CST Microwave Studio®, a three dimensional electromagnetic simulation tool developed by CST Computer Simulation Technology AG, to yield a desired, localized specific absorption rate (SAR) pattern. Feed connector 210 is generally circular and has a height 304. To simplify fabrication, a diameter of feed connector 210 may be the same as a diameter of center conductor 200 and/or as a diameter of the wire that is used to create the plurality of helical turns 212. The input impedance at feed end 219 of feed connector 210 is used to design first impedance matching structure 104a. For example, the input impedance can be computed using CST Microwave Studio®, another electromagnetic simulation tool, or measured experimentally. Height 304 may be determined by the electromagnetic simulation tool based on its effect on the desired high input impedance.

First capacitive section 220 has a first length 306. Inductive section 222 has a second length 308. Second capacitive section 224 has a third length 310. Conductive shield 204 has an inner diameter 312 and an outer diameter 314. Second conductive material 226 has an inner diameter 316. Third conductive material 230 has an inner diameter 318.

In the illustrative embodiment, first impedance matching structure 104a is a transmission line implementation of a π network of reactive elements as shown with reference to an equivalent circuit model 320. Coaxial cable 102 is modeled as a coaxial transmission line having characteristic impedance 322. First capacitive section 220 is modeled as a capacitor having a first capacitance 324. Inductive section 222 is modeled as an inductor having an inductance 326. Second capacitive section 224 is modeled as a capacitor having a second capacitance 328.

As discussed previously, first capacitive section 220 and second capacitive section 224 may be formed using low-impedance coaxial-cable sections by inserting a hollow copper tube in the region between center conductor 200 and conductive shield 204 of coaxial cable 102. The hollow copper tube is electrically connected to an inner surface of conductive shield 204 to form a new outer conductor with reduced inner diameters 316 and 318. This increases the capacitance per unit length of coaxial cable 102. Inductive section 222 may be formed using a section of coaxial cable 102 in which dielectric material 202 is removed to decrease the capacitance per unit length of the line.

The inductance per unit length of inductive section 222 can be increased by reducing a diameter of center conductor 200 along the length of inductive section 222 to achieve inductance 326 with a shorter length of transmission line. First capacitive section 220 and second capacitive section 224 further may be formed using the same or a different dielectric material that has a higher dielectric constant than the removed dielectric material 202 between center conductor 200 and conductive material 226 and between center conductor 200 and third conductive material 230, respectively. This further increases the capacitance per unit length of first capacitive section 220 and second capacitive section 224 to achieve first capacitance 324 and second capacitance 328 with a shorter length of transmission line.

The values of first capacitance 324, inductance 326, and second capacitance 328 are chosen to provide an impedance match between first antenna 106a and coaxial cable 102.

First length 306 of first capacitive section 220 may be estimated assuming a short transmission line approximation and using $$C_1 \ln\left(\frac{b_1}{a}\right) / 2\pi\epsilon_1,$$

where $C_1$ is first capacitance 324, $b_1$ is inner diameter 316 of second conductive material 226, a is the diameter of center conductor 200, and $\epsilon_1$ is a permittivity of the dielectric material between center conductor 200 and second conductive material 226.

Second length 308 of inductive section 222 may be estimated assuming a short transmission line approximation and using $$2\pi L/\mu \ln\left(\frac{b}{a}\right),$$

where L is inductance 326, b is inner diameter 312 of conductive shield 204, and μ is a permeability of second dielectric material 228.

Third length 310 of second capacitive section 224 may be estimated assuming a short transmission line approximation and using $$C_2 \ln\left(\frac{b_2}{a}\right) / 2\pi\epsilon_2,$$

where $C_2$ is second capacitance 328, $b_2$ is inner diameter 318 of third conductive material 230, and $\epsilon_2$ is a permittivity of the dielectric material between center conductor 200 and third conductive material 230. In an illustrative embodiment, first length 306, second length 308, and third length 310 may be calculated using the parameters above and finely tuned using full wave electromagnetic (EM) simulations in CST Microwave Studio® or another EM simulation tool.

Figure 3B:
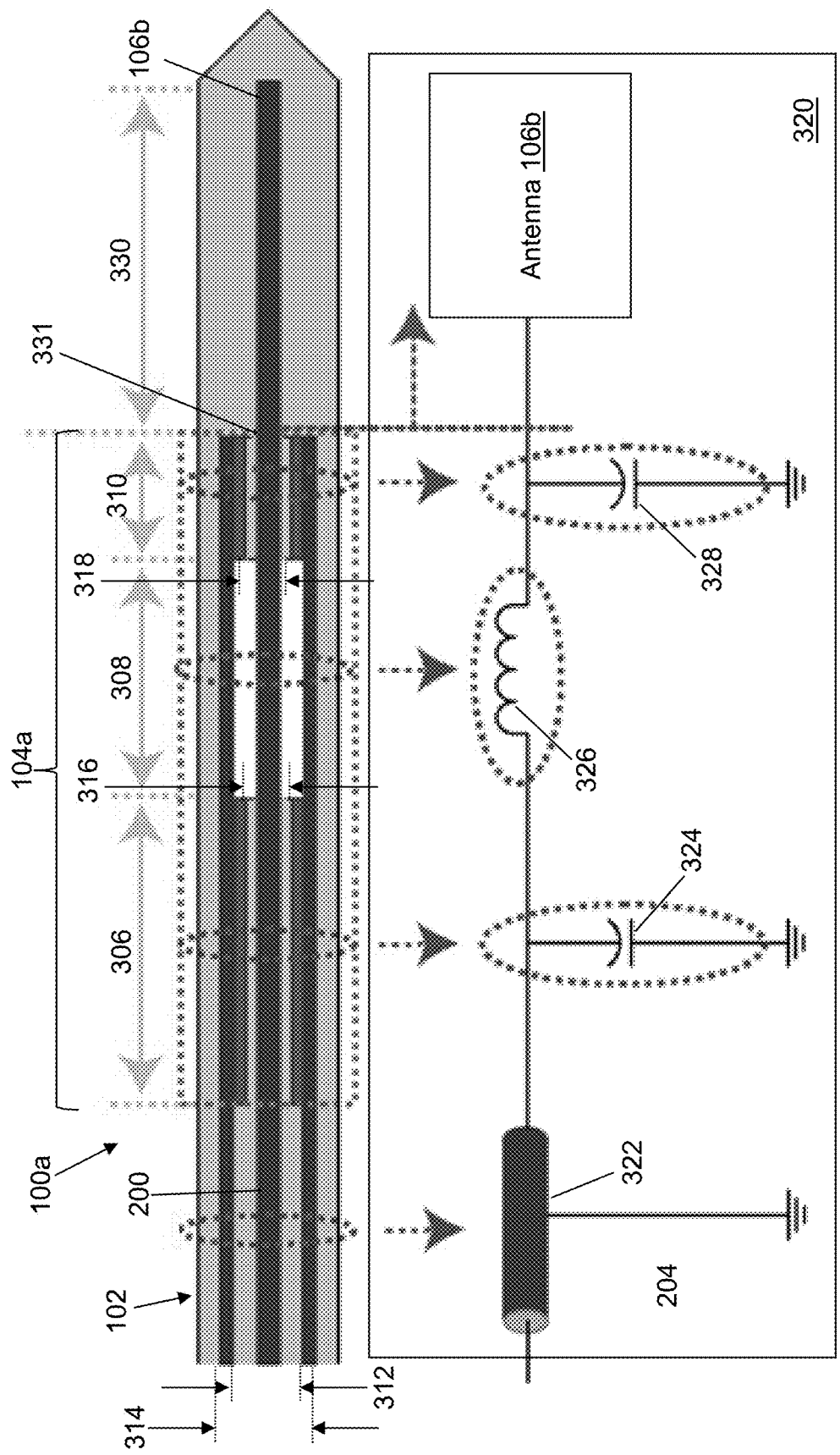
FIG. 3b depicts a view of a second MWA antenna system and an equivalent circuit model of the second MWA antenna system in accordance with an illustrative embodiment.

Referring to FIG. 3b, a second antenna 106b is a monopole antenna formed of conducting wire having a length 330. Length 330 can be determined, for example, using CST Microwave Studio®, a three dimensional electromagnetic simulation tool developed by CST Computer Simulation Technology AG, to yield a desired, localized specific absorption rate (SAR) pattern. A cross section of second antenna 106b may be circular, square, elliptical, rectangular, etc. A base 331 of second antenna 106b is mounted to and extends from center conductor 200. To simplify fabrication, a cross section of second antenna 106b may be the same as that of center conductor 200. The input impedance at base 331 of second antenna 106b is used to design first impedance matching structure 104a.

Second antenna 106b has an electrical length of half a wavelength at the selected operating frequency. At the selected operating frequency where the electrical length of second antenna 106b is approximately half a wavelength, an electric current at base 331 of second antenna 106b achieves a minimum while the voltage is maximized resulting in a high input impedance that creates a natural choke point for the currents that tend to flow on the outer surface of conductive shield 204 of coaxial cable 102 eliminating the need to use a balun. Despite the high feed-point impedance, matching between second antenna 106b and coaxial cable 102 can be achieved using first impedance matching structure 104a.

Figure 3C:
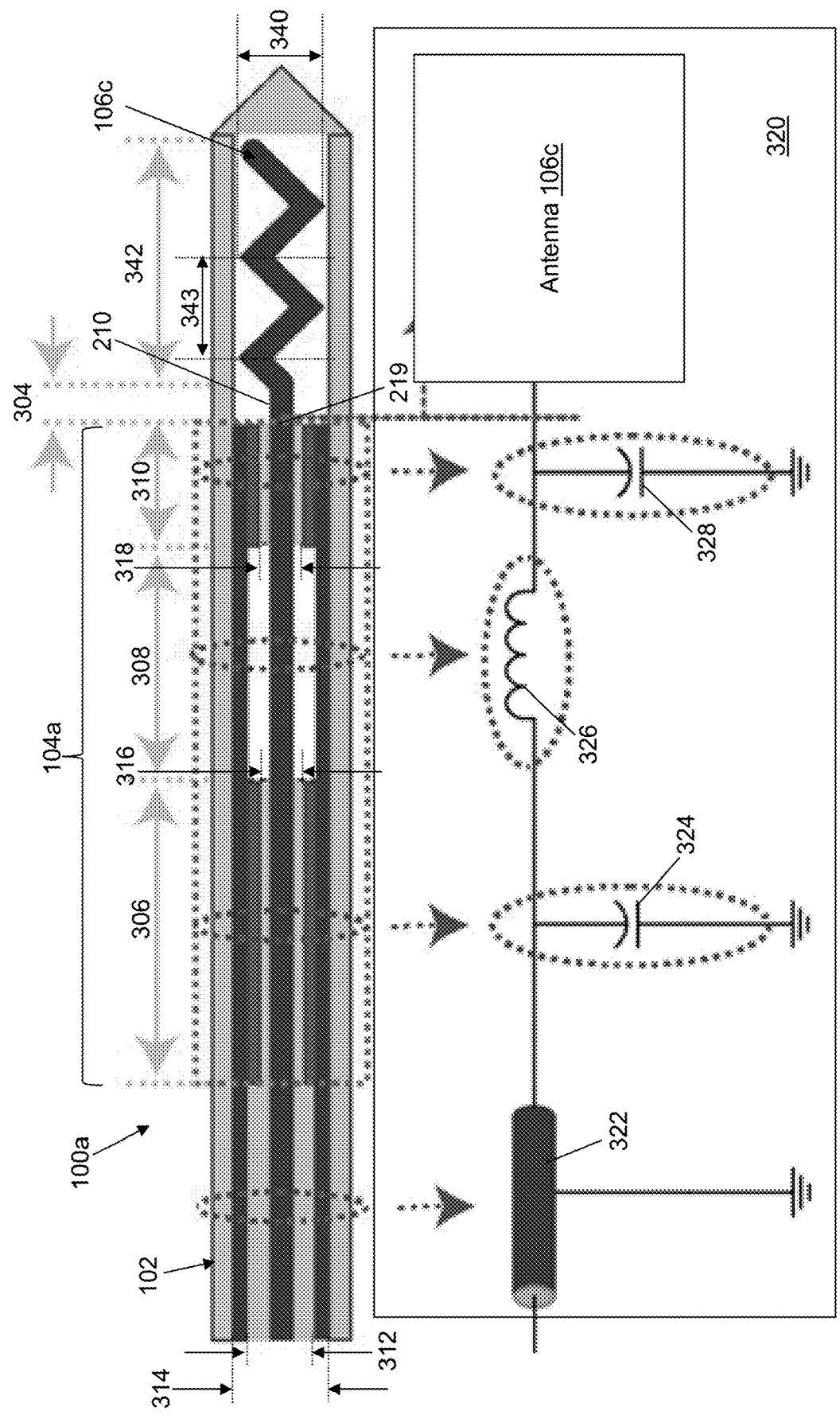
FIG. 3c depicts a view of a third MWA antenna system and an equivalent circuit model of the third MWA antenna system in accordance with an illustrative embodiment.

Referring to FIG. 3c, a third antenna 106c is a bent wire antenna formed of a conducting wire bent to form a number of bends, n. Third antenna 106c has a width 340 and a total height 342. The dimensions of the bent wire (diameter and pitch 343) are small compared with the wavelength so that third antenna 106c acts similar to a monopole antenna. Third antenna 106c may include feed connector 210. The number of bends, n, are mounted to and extend from feed connector 210.

Width 340, total height 342, and the number of bends, n, can be determined, for example, using CST Microwave Studio®, a three dimensional electromagnetic simulation tool developed by CST Computer Simulation Technology AG, to yield a desired, localized specific absorption rate (SAR) pattern. To simplify fabrication, a cross section of feed connector 210 may be the same as a diameter of center conductor 200 and/or as a diameter of the wire that is used to create the number of bends, n. The input impedance at feed end 219 of feed connector 210 is used to design first impedance matching structure 104a. For example, the input impedance can be computed using CST Microwave Studio®, another electromagnetic simulation tool, or measured experimentally.

The number of bends, n, have an electrical length of half a wavelength at a selected operating frequency. At the selected operating frequency where the electrical length of the number of bends is approximately half a wavelength, an electric current at feed end 219 of feed connector 210 achieves a minimum while the voltage is maximized. The resulting high input impedance creates a natural choke point for the currents that tend to flow on the outer surface of conductive shield 204 of coaxial cable 102 eliminating the need to use a balun. Despite the high feed-point impedance, matching between third antenna 106c and coaxial cable 102 can be achieved using first impedance matching structure 104a.

Figure 3D:
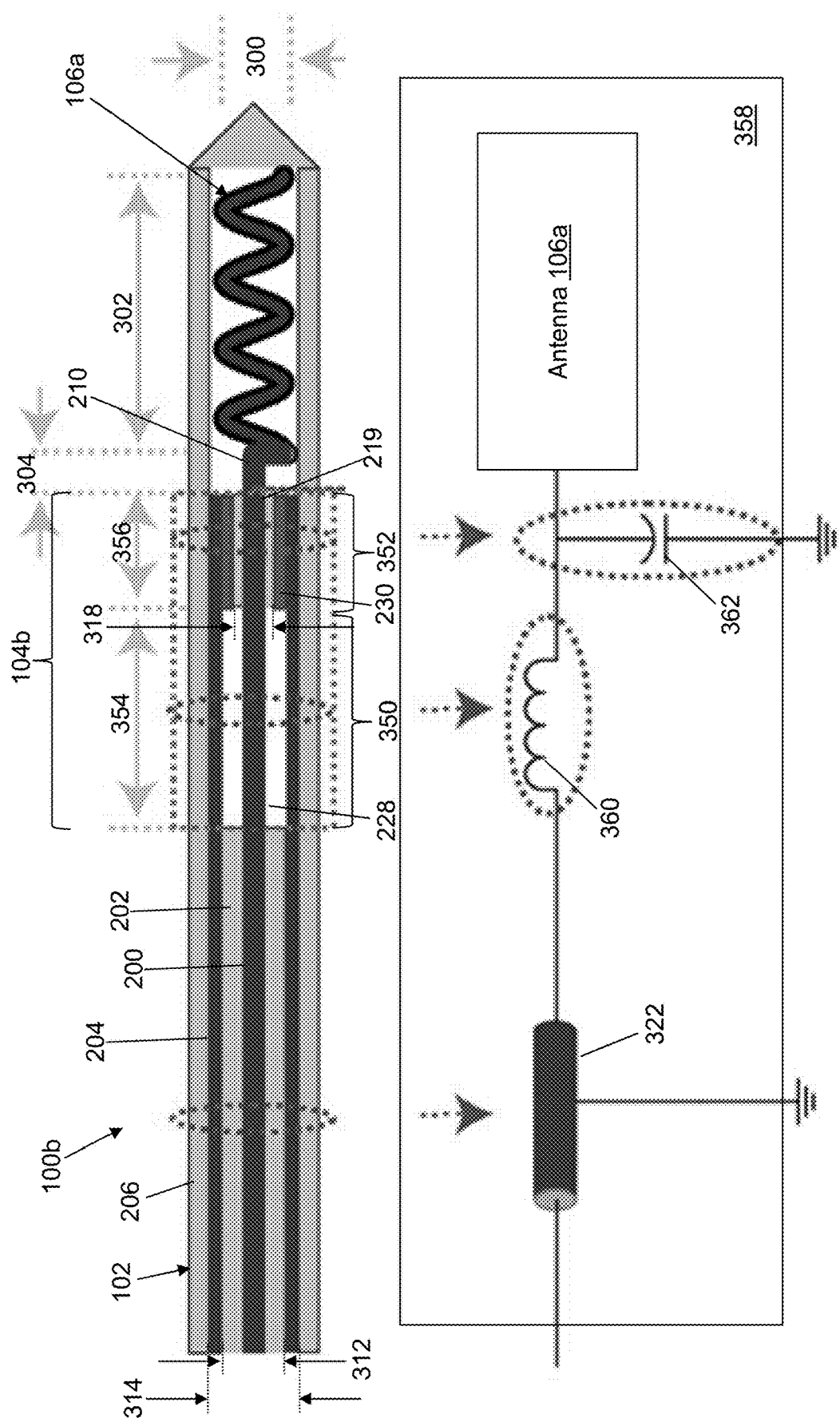
FIG. 3d depicts a view of a fourth MWA antenna system and an equivalent circuit model of the fourth MWA antenna system in accordance with an illustrative embodiment.

First impedance matching structure 104a may include additional or fewer capacitive sections and additional inductive sections in alternative embodiments. For example, a second inductive section may be mounted to the left of first capacitive section 220. As another example, referring to FIG. 3d, a second antenna system 100b is shown in accordance with an illustrative embodiment. Second antenna system 100b may include coaxial cable 102, a second impedance matching structure 104b, and first antenna 106a.

Second impedance matching structure 104b is mounted between coaxial cable 102 and feed end 219 of feed connector 210 of first antenna 106a. Second impedance matching structure 104b may include a second inductive section 350 and a third capacitive section 352. Second impedance matching structure 104b may be formed from an extension of coaxial cable 102. Second inductive section 350 and third capacitive section 352 may include center conductor 200 extending a length of second inductive section 350 and third capacitive section 352. Feed connector 210 is electrically connected to center conductor 200 extending from third capacitive section 352.

Dielectric material 202 surrounding center conductor 200 may be removed along a fourth length 354 of second inductive section 350 and replaced with second dielectric material 228 having a lower dielectric constant than dielectric material 202. Conductive shield 204 surrounds second dielectric material 228 along fourth length 354 of second inductive section 350 and insulating jacket 206 surrounds conductive shield 204 along fourth length 354 of second inductive section 350.

Third capacitive section 352 further may include dielectric material 202 surrounding center conductor 200 along a fifth length 356 of third capacitive section 352, conductive shield 204 surrounding dielectric material 202 along fifth length 356 of third capacitive section 352, and insulating jacket 206 surrounding conductive shield 204 along fifth length 356 of third capacitive section 352. A portion of dielectric material 202 may be removed along fifth length 356 of third capacitive section 352 adjacent conductive shield 204. Third conductive material 230 is inserted to replace the removed portion of dielectric material 202. In an alternative embodiment, all of dielectric material 202 is removed along fifth length 356 of third capacitive section 352 adjacent conductive shield 204, and third conductive material 230 is inserted to replace a portion of the removed dielectric material 202 and a different, or the same, dielectric material is inserted to replace the remaining portion of the removed dielectric material 202.

Second impedance matching structure 104b is a transmission line implementation of reactive elements as shown with reference to an equivalent circuit model 358. Coaxial cable 102 is modeled as a coaxial transmission line having characteristic impedance 322. Second inductive section 350 is modeled as an inductor having a second inductance 360. Third capacitive section 352 is modeled as a capacitor having a third capacitance 362. Second inductance 360 and third capacitance 362 are chosen to provide an impedance match between first antenna 106a and coaxial cable 102.

Fourth length 354 of second inductive section 350 may be estimated assuming a short transmission line approximation and using $$2\pi L/\mu \ln\left(\frac{b}{a}\right),$$

where L is second inductance 360. Fifth length 356 of third capacitive section 352 may be estimated assuming a short transmission line approximation and using $$C_2 \ln\left(\frac{b_2}{a}\right)/2\pi\epsilon_2,$$

where $C_2$ is third capacitance 362. In an illustrative embodiment, fourth length 354 and fifth length 356 may be calculated using the parameters above and finely tuned using full wave electromagnetic (EM) simulations in CST Microwave Studio® or another EM simulation tool.

Figure 4:
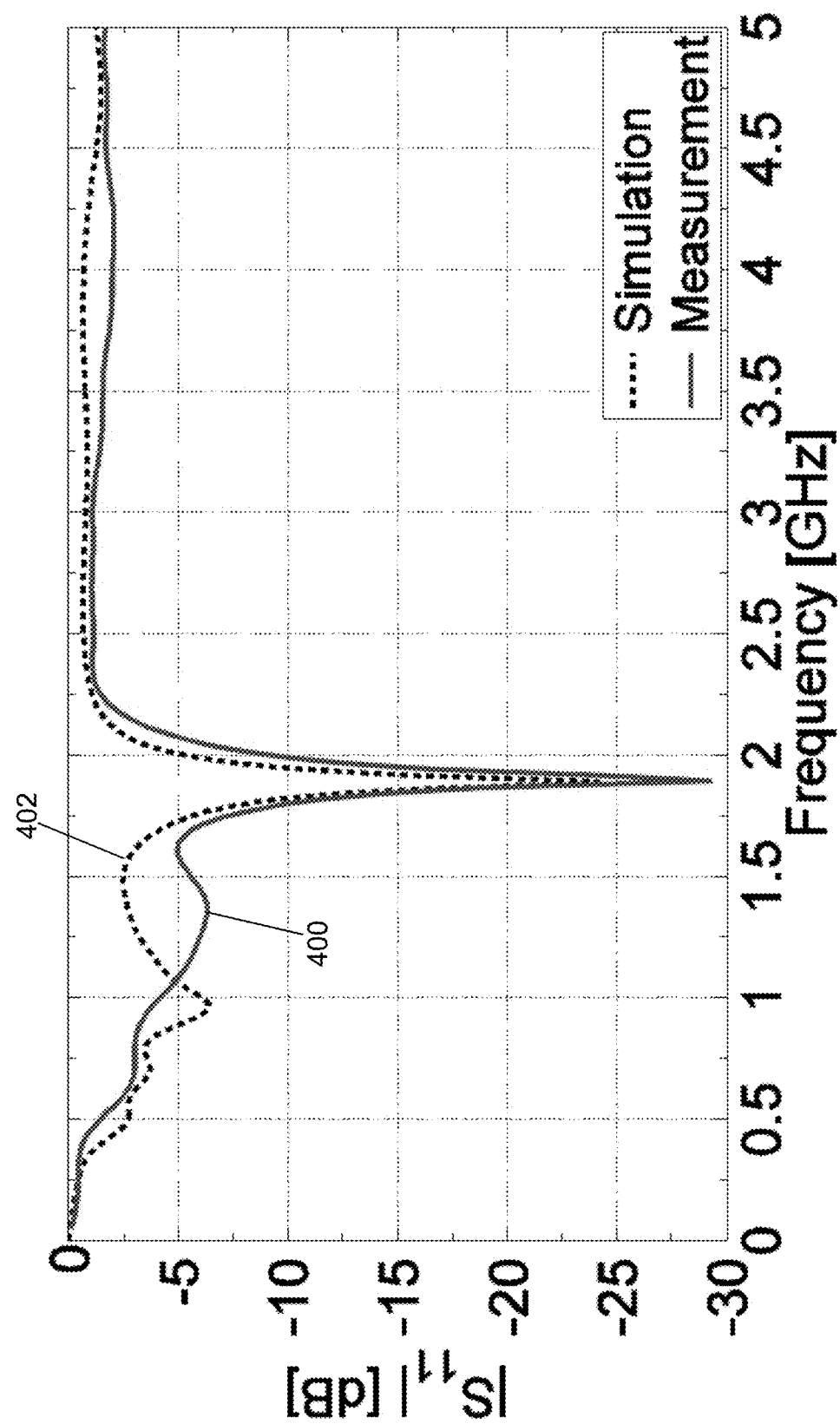
FIG. 4 shows a comparison between a simulated and a measured input impedance, $S_{11}$, of the MWA antenna system of FIG. 2 in accordance with an illustrative embodiment.

Referring to FIG. 4, a comparison between simulated and measured input impedance, $S_{11}$, of first antenna system 100a is shown in accordance with an illustrative embodiment. The simulated results assumed liver tissue; whereas, the measured results were obtained using a reference material that mimics liver tissue. A first curve 400 shows the measured input impedance $S_{11}$. A second curve 402 shows the simulated input impedance $S_{11}$.

An operating frequency $f_o$ of first antenna 106a was selected as 1.9 GHz. Design parameters for first antenna 106a were diameter 300 equal 1.6 millimeters (mm), total height 302 equal 20 mm, height 304 equal 2 mm, and n equal 10 turns. Characteristic impedance 322 of coaxial cable 102 was 50 ohms. Design parameters for first capacitive section 220 were first length 306 equal 22 mm, a equal 0.574 mm, $b_1$ equal 0.876 mm of copper tubing, and $\in_1$ is the permittivity of polytetrafluoroethylene. Design parameters for second capacitive section 224 were third length 310 equal 6 mm, a equal 0.574 mm, $b_2$ equal 0.876 mm of copper tubing, and $\in_1$ is the permittivity of Teflon® (polytetrafluoroethylene). Design parameters for inductive section 222 were second length 308 equal 18 mm, a equal 0.574 mm, b equal 1.676 mm of copper tubing, and μ is the permeability of air.

Coaxial cable 102 consisted of 50Ω UT-085C-LL semi-rigid coaxial cable with a maximum outer diameter of 2.197 mm. First antenna 106a was placed in a Teflon® catheter with an outer diameter of 3.2 mm. The relatively large dimensions were chosen to simplify the fabrication process during the proof-of-concept demonstration phase. The outer diameter of first antenna 106a can be significantly reduced with a proper choice of a smaller coaxial cable 102 and a correspondingly thinner catheter. The dimensions of the helical antenna and matching section indicated in the preceding paragraph were optimized to provide good impedance matching and a localized SAR pattern at 1.9 GHz.

First curve 400 of the fabricated antenna was measured using a vector network analyzer when first antenna 106a was inserted in a 45:55 mixture of methanol and deionized water, whose relative permittivity at 1.9 GHz matches the liver tissue assumed in the simulation. The prototype was initially fabricated with the same dimensions as those determined in the simulations. However, a slight shift in the operating frequency was observed. Specifically, first antenna 106a was matched at 2.05 GHz instead of 1.90 GHz. This was attributed to the non-idealities that exist in the fabricated prototype (e.g. slight deviation of the fabricated dimensions, air gaps in the Teflon® insulation layer of first capacitive section 220 and second capacitive section 224, etc.). This frequency shift, however, was eliminated in a second prototype, wherein first length 306 was increased from 22 mm to 24 mm and third length 310 was increased from 6 mm to 7 mm. The measured S11 of this prototype is shown in second curve 402 and shows excellent impedance matching at 1.9 GHz. In both prototypes, the S11 measurements were stable as the insertion depth of first antenna 106a was changed indicating that no currents are excited on conductive shield 204.

Figure 5:
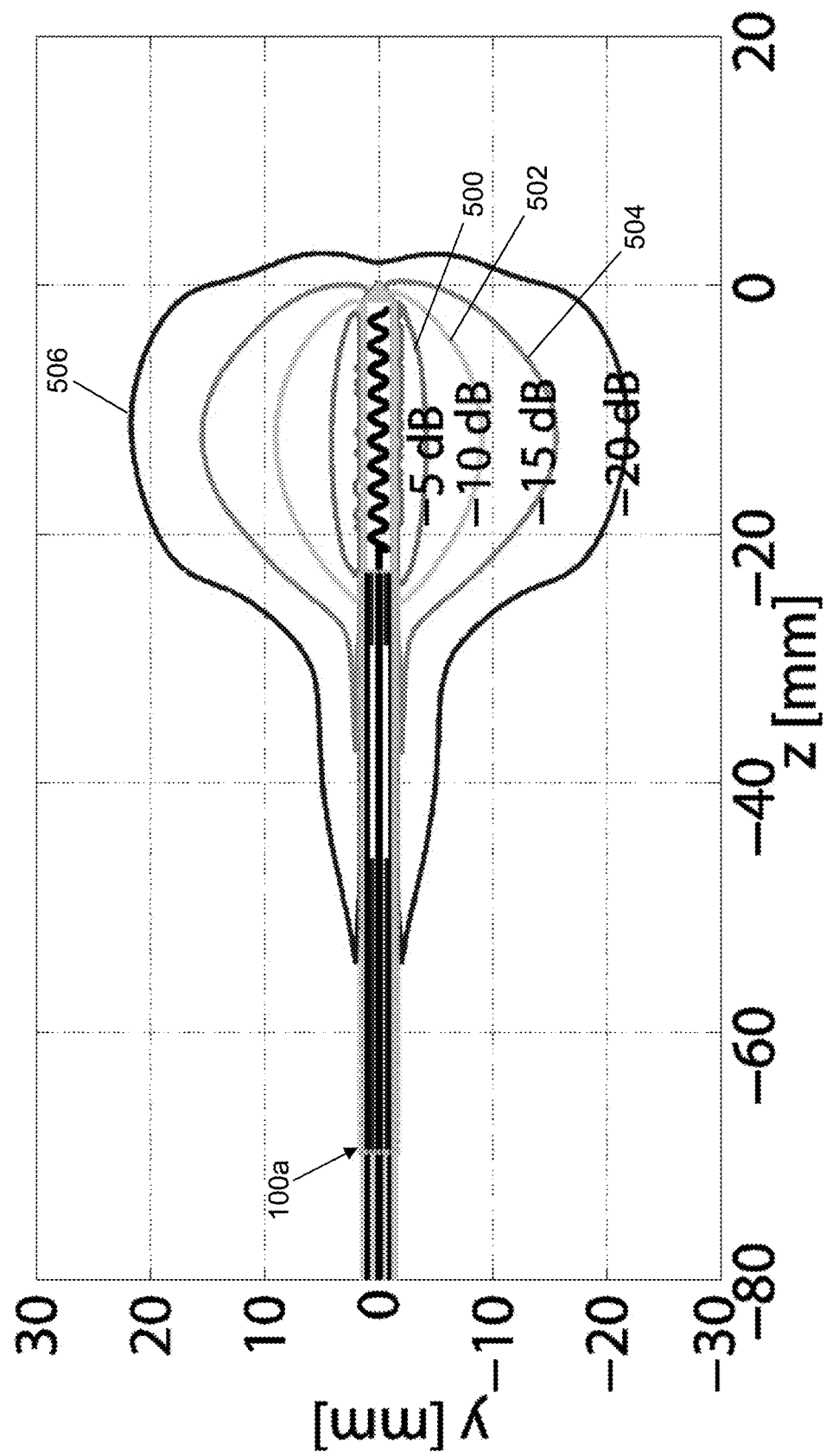
FIG. 5 shows a simulated specific absorption rate (SAR) pattern of the MWA antenna system of FIG. 2 in liver tissue in accordance with an illustrative embodiment.

Referring to FIG. 5, a simulated normalized SAR pattern of first antenna 106a inserted into liver tissue at the insertion depth of 85 mm is shown. The simulated normalized SAR pattern includes a −5 dB curve 500, a −10 dB curve 502, a −15 dB curve 504, and a −20 dB curve 506. The SAR levels are reduced by more than 20 dB compared to a maximum SAR value at a longitudinal distance of 60 mm from the tip of first antenna 106a. The localization of the SAR pattern indicates that the currents excited on conductive shield 204 of coaxial cable 102 are effectively suppressed by the high input impedance at feed connector 210 of first antenna 106a.

The balun is eliminated by using first antenna 106a at a frequency where its input impedance is very high, which effectively chokes the currents on an outer surface of coaxial cable 102 and acts as a natural balun. Despite the high feed-point impedance, first impedance matching structure 104a is used to achieve impedance matching between first antenna 106a and coaxial cable 102. The simulated SAR pattern of first antenna 106a verifies localized heating potential at the desired frequency of operation. First antenna system 100a offers a practical solution to decrease an overall diameter of coax-fed interstitial antennas and to reduce the invasiveness of the MWA treatment.

Figure 6:
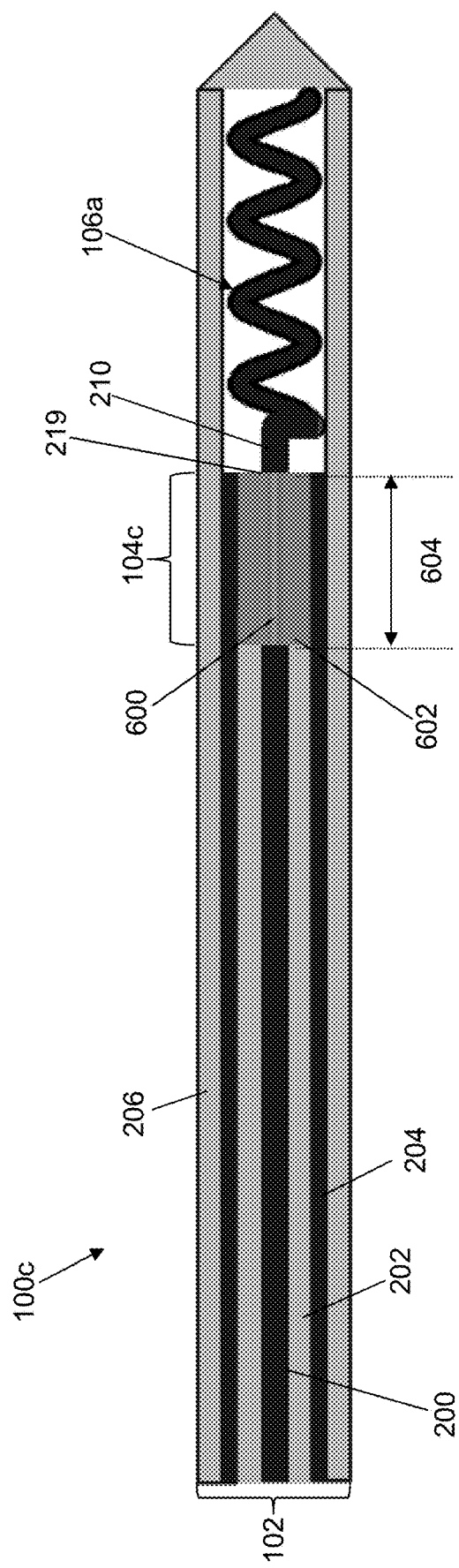
FIG. 6 depicts a side cross sectional view of a second MWA antenna system of FIG. 1 in accordance with an illustrative embodiment.

With reference to FIG. 6, a side cross-sectional view of a third antenna system 100c is shown in accordance with an illustrative embodiment. Third antenna system 100c may include coaxial cable 102, a third impedance matching structure 104c, and first antenna 106a. Third impedance matching structure 104c is configured to match the impedance of coaxial cable 102 to the impedance of first antenna 106a. Third impedance matching structure 104c may be formed from an extension of coaxial cable 102. Third impedance matching structure 104c may include a second center conductor 600, a third dielectric material 602, conductive shield 204, and insulating jacket 206. Feed connector 210 is electrically connected to second center conductor 600. Third impedance matching structure 104c is mounted between coaxial cable 102 and feed end 219 of feed connector 210 of first antenna 106a.

Third dielectric material 602 surrounds second center conductor 600 along a length 604 of third impedance matching structure 104c, conductive shield 204 surrounds third dielectric material 602 along length 604 of third impedance matching structure 104c, and insulating jacket 206 surrounds conductive shield 204 along length 604 of third impedance matching structure 104c.

Second center conductor 600 may be formed by removing a portion of the diameter of center conductor 200. Dielectric material 202 surrounding center conductor 200 is removed along length 604 of third impedance matching structure 104c and replaced with third dielectric material 602 having a lower dielectric constant than dielectric material 202. In an illustrative embodiment, third dielectric material 602 is air. In an illustrative embodiment, length 604 is a quarter-wavelength.

Third impedance matching structure 104c may be modeled as a transformer. The characteristic impedance of third impedance matching structure 104c may be determined from $$Z' = \frac{1}{2\pi}\sqrt{\mu/\varepsilon}\ln\frac{b}{a'},$$

where b is inner diameter 312 of conductive shield 204, a' is the diameter of second center conductor 600, μ is a permeability of third dielectric material 602, and E is a permittivity of third dielectric material 602. $Z' = \sqrt{Z_0 Z_{in}}$, where $Z_0$ is characteristic impedance 322 of coaxial cable 102, and $Z_{in}$ is the input impedance of first antenna 106a at feed end 219 of feed connector 210. The diameter of second center conductor 600 may be determined as $$a' = \frac{b}{e^{Z'2\pi\sqrt{\frac{\varepsilon}{\mu}}}}.$$

Figure 7:
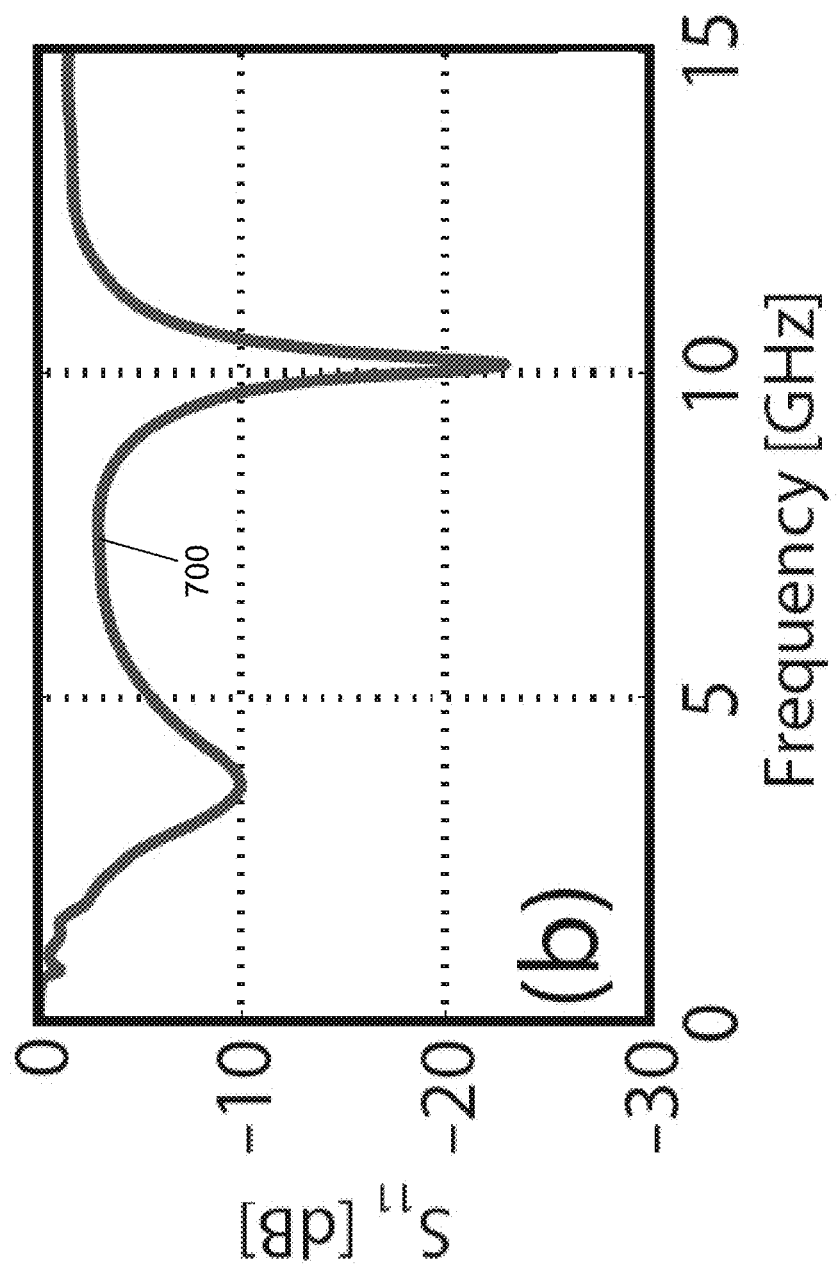
FIG. 7 shows a simulated input impedance, $S_{11}$, of the MWA antenna system of FIG. 6 in liver tissue in accordance with an illustrative embodiment.

Referring to FIG. 7, a simulated input impedance, $S_{11}$, of third antenna system 100c in liver tissue is shown in accordance with an illustrative embodiment. A curve 700 shows the simulated input impedance $S_{11}$. An operating frequency $f_o$ of first antenna 106a was selected as 10 GHz. Design parameters for first antenna 106a were diameter 300 equal 2.2 mm, total height 302 equal 2 mm, height 304 equal 0.75 mm, and n equal $$1\frac{1}{8}$$

turns. Characteristic impedance 322 of coaxial cable 102 was 50 ohms. Design parameters for third impedance matching structure 104c were length 604 equal 5 mm, a equal 0.512 mm, b equal 1.676 mm, the diameter of second center conductor 600 equal 0.18 mm, and μ is the permeability of air. The simulated S11 shown in curve 700 shows excellent impedance matching at 10 GHz.

Figure 8:
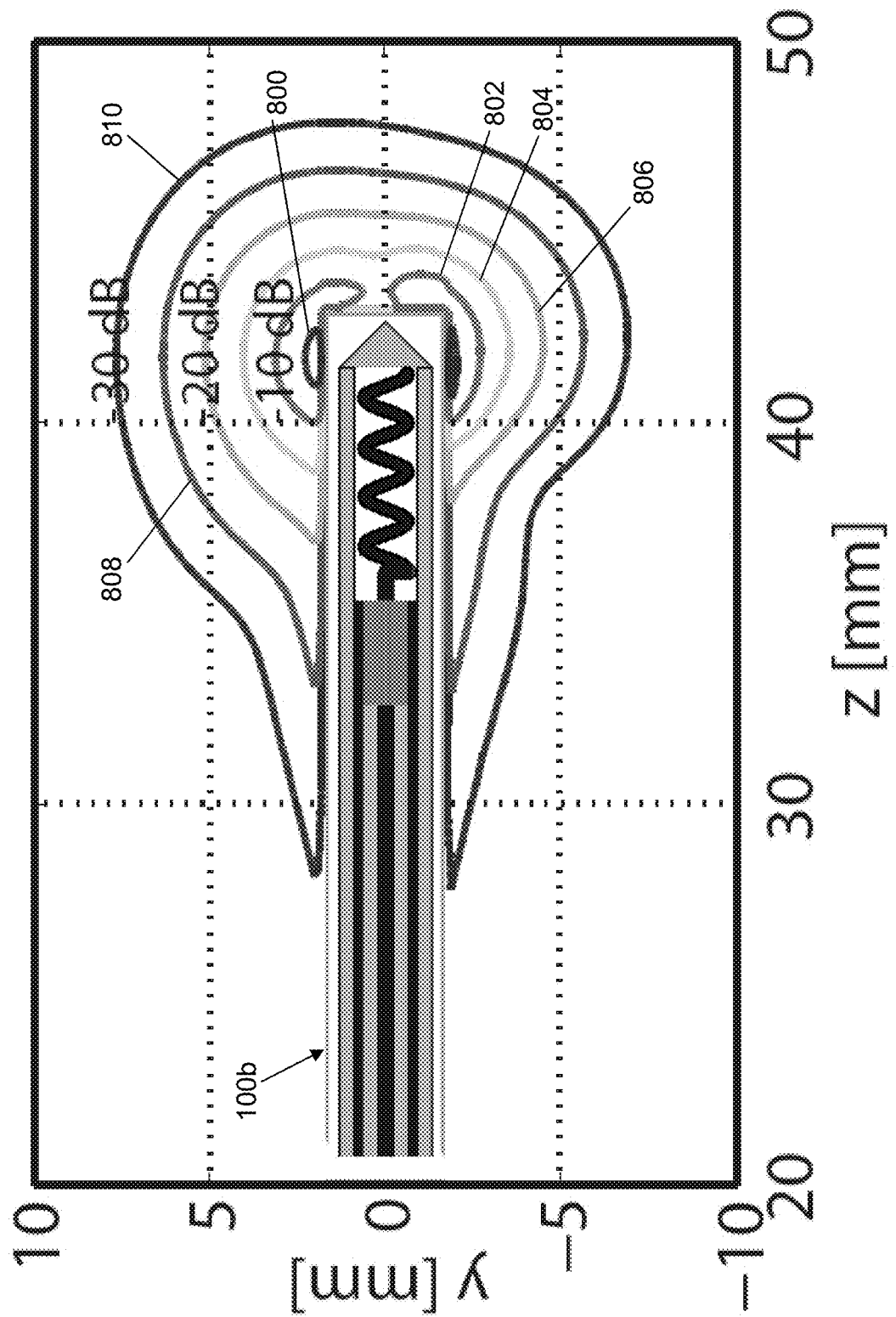
FIG. 8 shows a simulated SAR pattern of the MWA antenna system of FIG. 6 in the liver tissue in accordance with an illustrative embodiment.

Referring to FIG. 8, a simulated normalized SAR pattern of first antenna 106a of third antenna system 100c inserted into liver tissue at an insertion depth of 53 mm is shown. The simulated normalized SAR pattern includes a −5 dB curve 800, a −10 dB curve 802, a −15 dB curve 804, a −20 dB curve 806, a −25 dB curve 808, and a −30 dB curve 810. The SAR levels are reduced by more than 30 dB compared to a maximum SAR value at a longitudinal distance of 15 mm from the tip of first antenna 106a. The localization of the SAR pattern indicates that the currents excited on conductive shield 204 of coaxial cable 102 are effectively suppressed by the high feed point impedance of the antenna.

Figure 9:
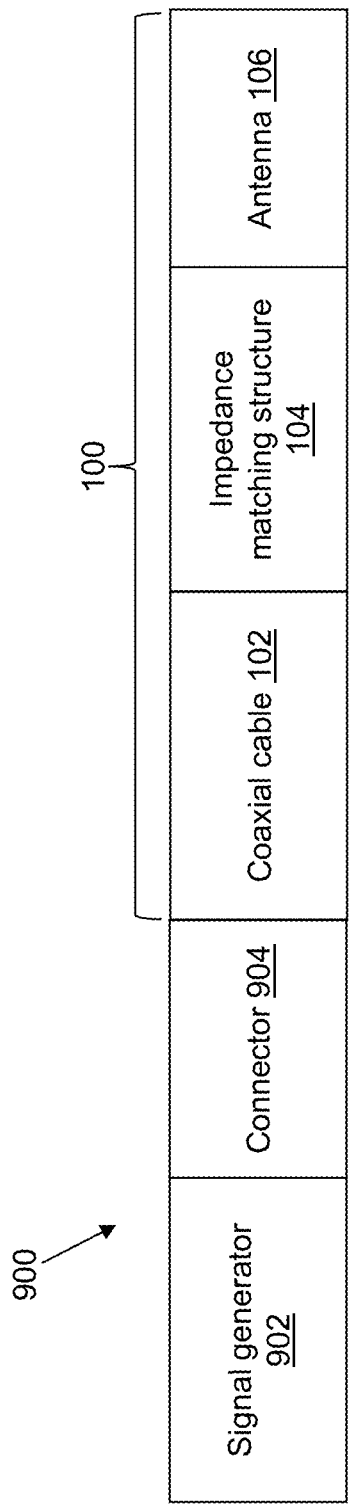
FIG. 9 depicts a block diagram of a transmitter incorporating the MWA antenna system of FIG. 1 in accordance with an illustrative embodiment.

Referring to FIG. 9, a block diagram of a transmitter 900 is shown in accordance with an illustrative embodiment. Transmitter 900 may include a signal generator 902, a connector 904, and antenna system 100. Signal generator 902 generates an analog signal at the operating frequency selected for antenna system 100. A duty cycle of the analog signal may be controlled by signal generator 902 based, for example, on an ablation zone size and heating rate. Connector 904 connects a second end of coaxial cable 102 opposite the end of center conductor 200 that mounts to impedance matching structure 104 to signal generator 902. Connector 904 may be a coaxial connector designed to maintain the coaxial form across the connection and having the same impedance as coaxial cable 102. Antenna system 100 receives the analog signal with a matching impedance at a feed end and radiates an electromagnetic wave into the surrounding tissue.

Figure 10:
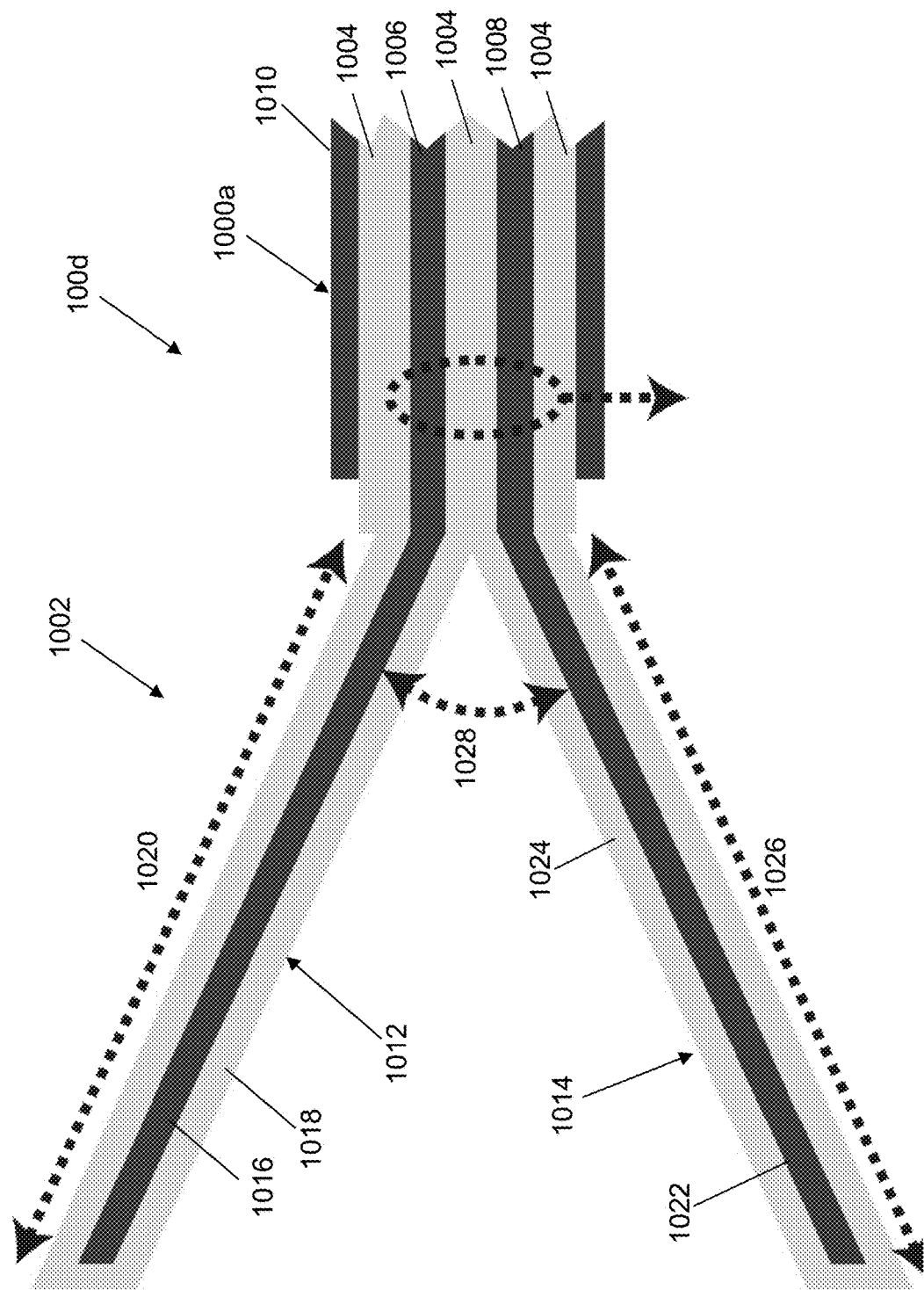
FIG. 10 depicts a side cross sectional view of a third MWA antenna system in accordance with an illustrative embodiment.

With reference to FIG. 10, a side cross-sectional view of a fourth antenna system 100d is shown in accordance with an illustrative embodiment. Fourth antenna system 100d may be used to perform MWA. Fourth antenna system 100d may include a two-wire balanced cable 1000 and a fourth antenna 1002. Two-wire balanced cable 1000 is a balanced transmission line composed of a two-conductor, balanced line enclosed by a floating shield. Two-wire balanced cable 1000 may include a dielectric material 1004, a first conductive line 1006, a second conductive line 1008, and a floating shield 1010. Floating shield 1010 may have a floating potential instead of being grounded.

Two-wire balanced cable 1000 may include any length of cable having any characteristic impedance. First conductive line 1006 and second conductive line 1008 are parallel to each other and extend along a length of two-wire balanced cable 1000. First conductive line 1006 and second conductive line 1008 may be formed of a solid conductive material such as copper plated steel, silver plated steel, silver plated copper, silver plated copper clad steel, copper, copper clad aluminum, steel, etc. Dielectric material 1004 may include foamed polyethylene, solid polyethylene, polyethylene foam, polytetrafluoroethylene, air, air space polyethylene, vacuum, etc. Dielectric material 1004 surrounds both first conductive line 1006 and second conductive line 1008 along the length of two-wire balanced cable 1000 to maintain a uniform spacing between first conductive line 1006 and second conductive line 1008. Floating shield 1010 can be made from many different conductive materials such as copper, aluminum, etc. Floating shield 1010 surrounds dielectric material 1004 along the length of two-wire balanced cable 1000.

A current flow in first conductive line 1006 is balanced by a current flow in second conductive line 1008. Floating shield 1010 contains the fields of first conductive line 1006 and second conductive line 1008 and ensures that the fields do not penetrate into the tissue surrounding floating shield 1010.

Fourth antenna 1002 may be any base fed balanced type antenna such as a dipole antenna, a loop antenna, etc. In the illustrative embodiment of FIG. 10, fourth antenna 1002 is a dipole antenna. Fourth antenna 1002 may include a first arm 1012 and a second arm 1014. First arm 1012 may include a third conductive line 1016 surrounded by a second dielectric material 1018 along a length 1020 of first arm 1012. Third conductive line 1016 may be an extension of first conductive line 1006, and second dielectric material 1018 may be an extension of dielectric material 1004. Second arm 1014 may include a fourth conductive line 1022 surrounded by a third dielectric material 1024 along a length 1026 of second arm 1014. Fourth conductive line 1022 may be an extension of second conductive line 1008, and third dielectric material 1024 may be an extension of dielectric material 1004. First arm 1012 and second arm 1014 extend from two-wire balanced cable 1000 at an angle 1028 formed between first arm 1012 and second arm 1014.

Figure 11:
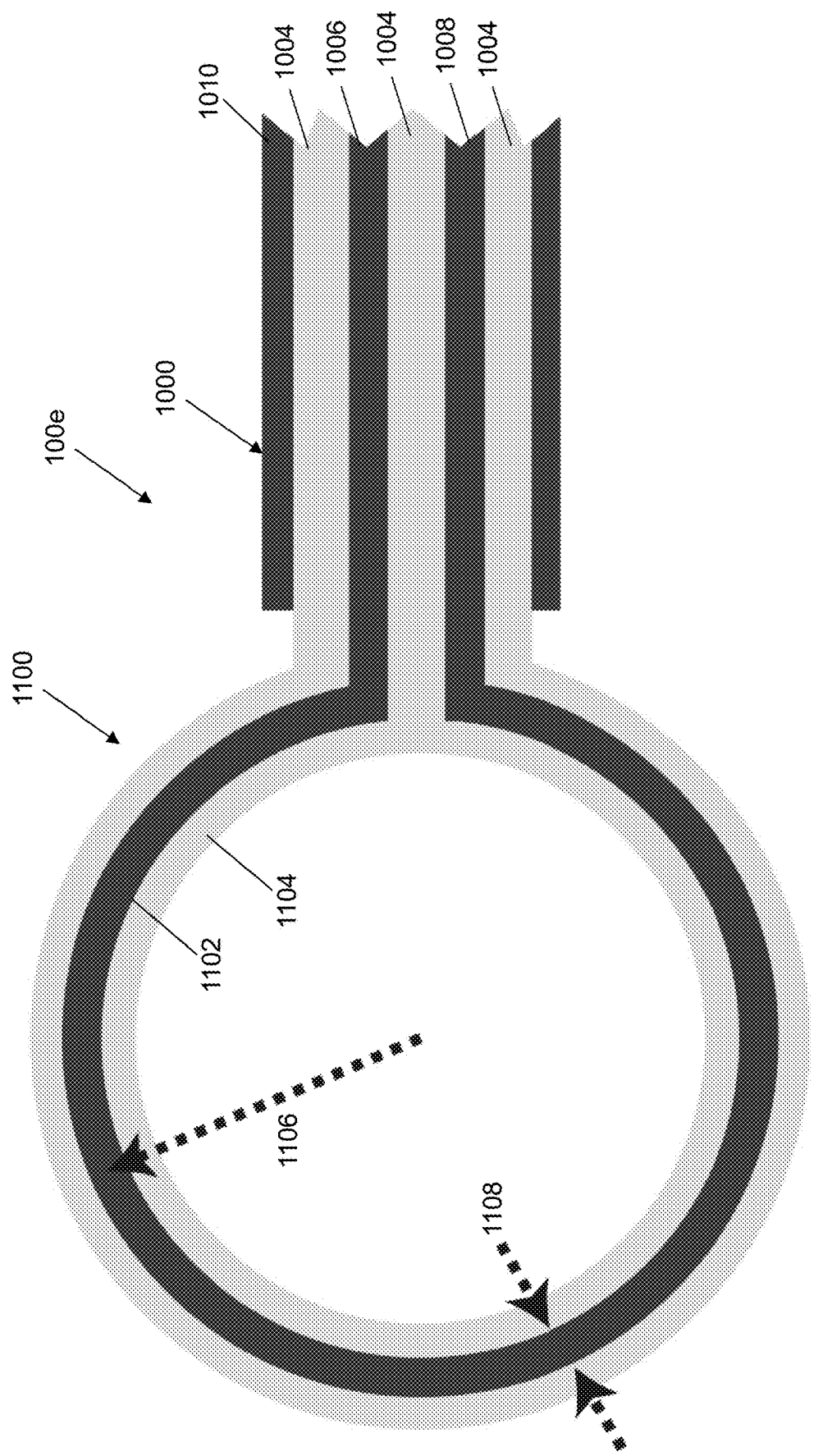
FIG. 11 depicts a side cross sectional view of a fourth MWA antenna system in accordance with an illustrative embodiment.

With reference to FIG. 11, a side cross-sectional view of a fifth antenna system 100e is shown in accordance with an illustrative embodiment. Fifth antenna system 100e may be used to perform MWA. Fifth antenna system 100e may include two-wire balanced cable 1000 and a fifth antenna 1100. In the illustrative embodiment of FIG. 11, fifth antenna 1100 is a loop antenna. Fifth antenna 1100 may include a fifth conductive line 1102 surrounded by a fourth dielectric material 1104. Fifth conductive line 1102 may connect between first conductive line 1006 and second conductive line 1008 of two-wire balanced cable 1000. Fourth dielectric material 1104 may be an extension of dielectric material 1004. Fifth conductive line 1102 has a radius 1106 and a width 1108.

Figure 12:
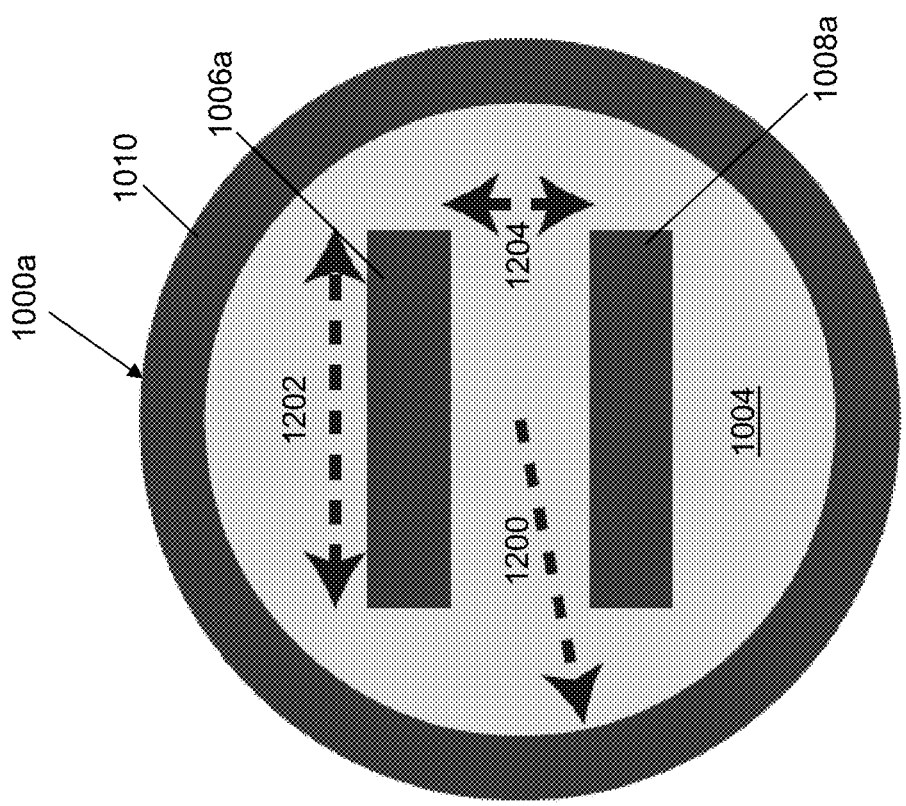
FIG. 12 depicts a front cross-sectional view of a two-wire transmission line of the third and/or fourth MWA antenna system of FIGS. 10 and 11 in accordance with an illustrative embodiment.

With reference to FIG. 12, a front cross-sectional view of a first two-wire balanced cable 1000a is shown in accordance with an illustrative embodiment. First two-wire balanced cable 1000a may include dielectric material 1004, a first conductive line 1006a, a second conductive line 1008a, and floating shield 1010. Dielectric material 1004 has a radius 1200. First conductive line 1006a and second conductive line 1008a are formed of rectangular strips having a width 1202 and separated by a distance 1204.

Figure 13:
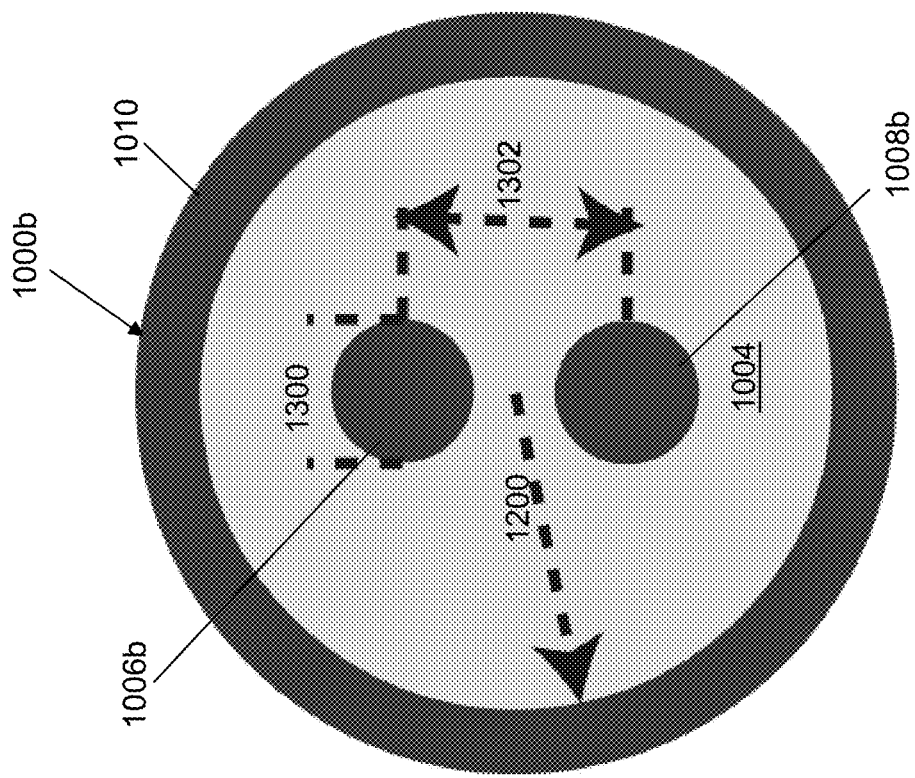
FIG. 13 depicts a front cross-sectional view of a second two-wire transmission line of the third and/or fourth MWA antenna system of FIGS. 10 and 11 in accordance with an illustrative embodiment.

With reference to FIG. 13, a front cross-sectional view of a second two-wire balanced cable 1000b is shown in accordance with an illustrative embodiment. Second two-wire balanced cable 1000b may include dielectric material 1004, a first conductive line 1006b, a second conductive line 1008b, and floating shield 1010. Dielectric material 1004 has radius 1200. First conductive line 1006b and second conductive line 1008b are formed of circular wires having a diameter 1300 and separated by a distance 1302.

Figure 14:
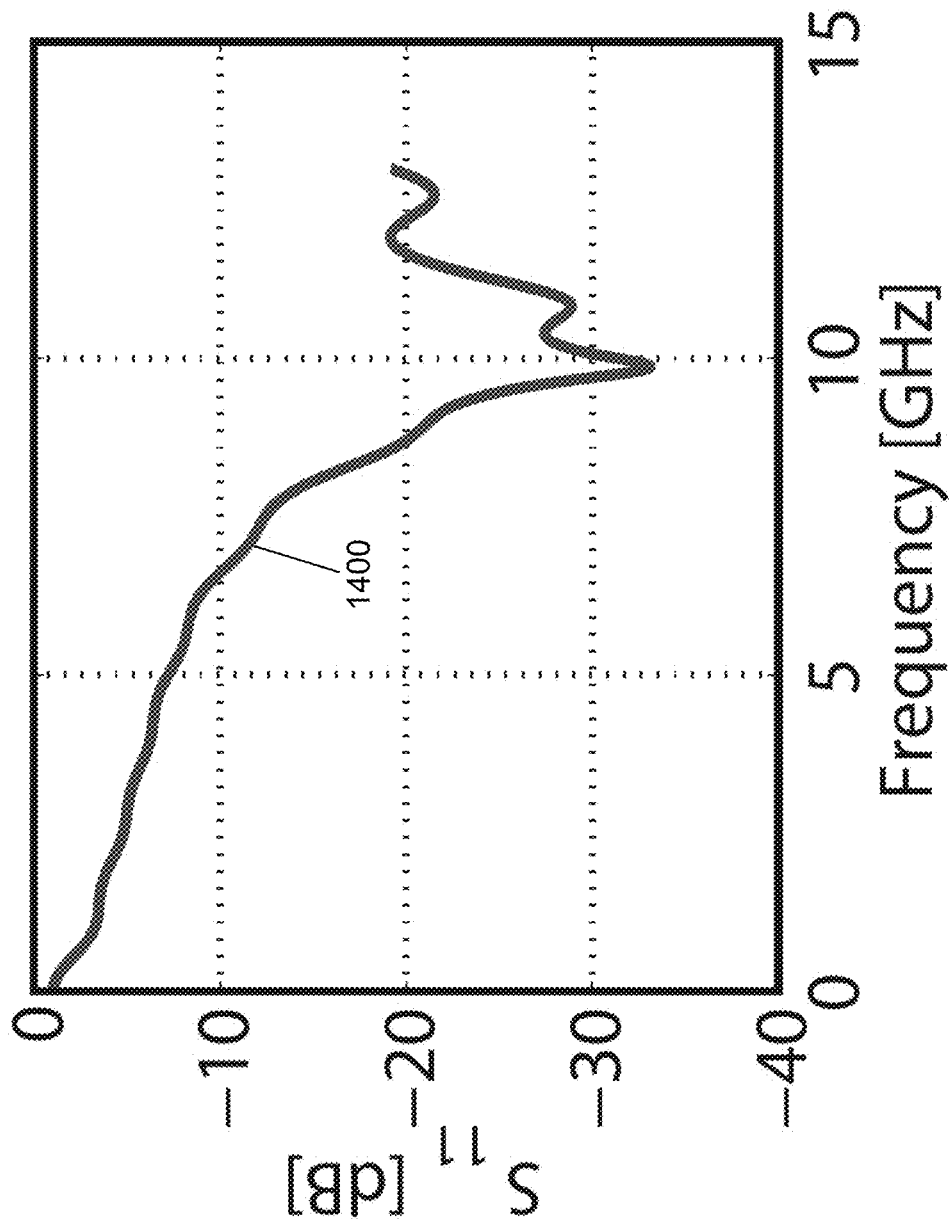
FIG. 14 shows a simulated input impedance, $S_{11}$, of the MWA antenna system of FIG. 10 in the liver tissue in accordance with an illustrative embodiment.

Referring to FIG. 14, a simulated input impedance, $S_{11}$, of fourth antenna system 100d in liver tissue is shown in accordance with an illustrative embodiment. A curve 1400 shows the simulated input impedance $S_{11}$. An operating frequency $f_o$ of fourth antenna 1002 was selected as 10 GHz. Fourth antenna 1002 was fed by first two-wire balanced cable 1000a. Design parameters for first two-wire balanced cable 1000a are radius 1200 equal 0.2 mm, width 1202 equal 0.3 mm, and distance 1204 equal 0.05 mm. Length 1020 of first arm 1012 and length 1026 of second arm 1014 were equal to 2 mm and angle 1028 between first arm 1012 and second arm 1014 was 20°. A full-wave EM simulation was conducted to predict the response of third antenna system 100c in liver tissue. The simulated S11 shown in curve 1400 shows excellent impedance matching at 10 GHz.

Figure 15:
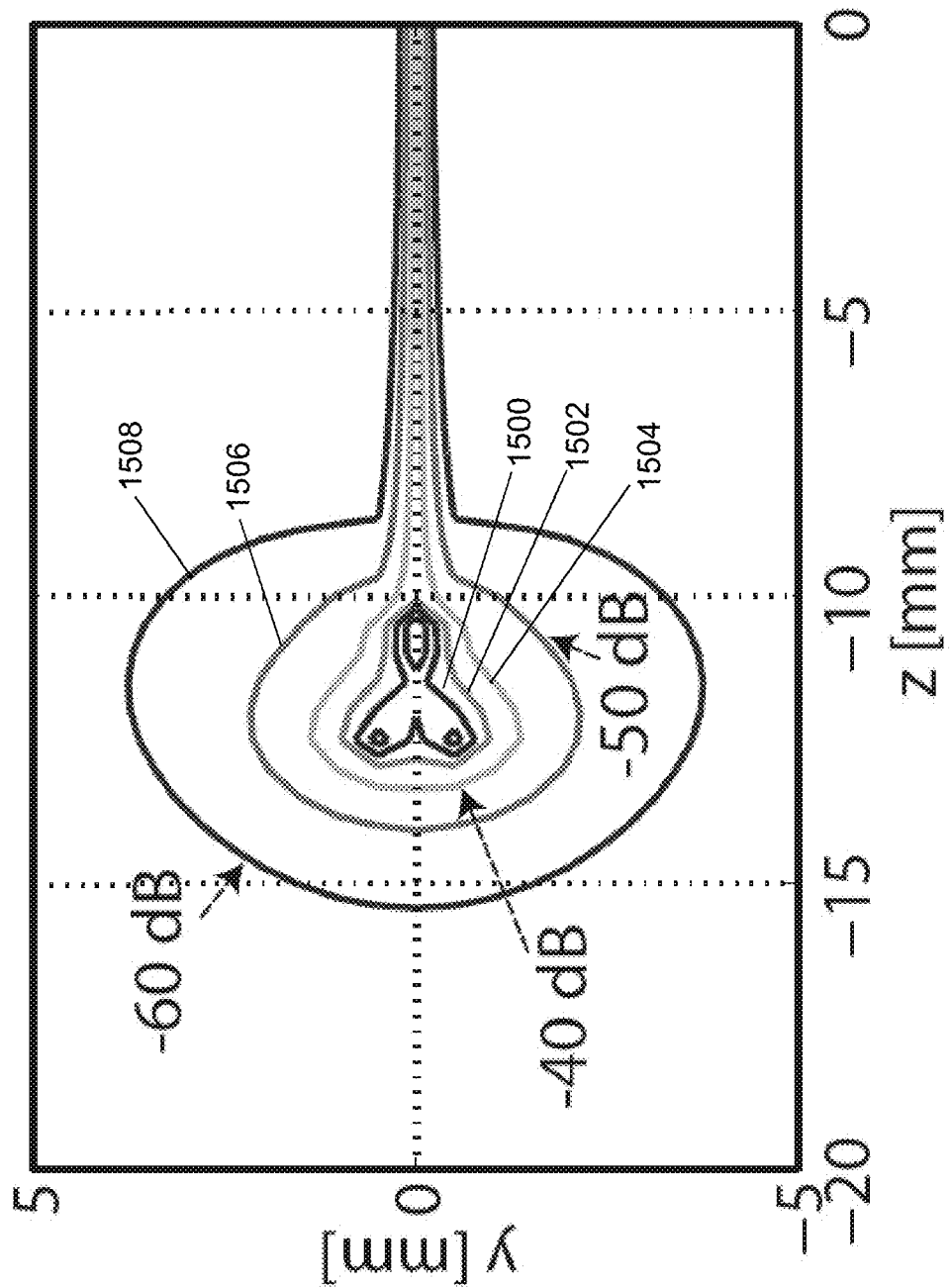
FIG. 15 shows a simulated SAR pattern of the MWA antenna system of FIG. 10 in the liver tissue in accordance with an illustrative embodiment.

Referring to FIG. 15, a simulated normalized SAR pattern of fourth antenna 1002 inserted into liver tissue at an insertion depth of 57 mm is shown. The simulated normalized SAR pattern includes a −20 dB curve 1500, a −30 dB curve 1502, a −40 dB curve 1504, a −50 dB curve 1506, and a −60 dB curve 1508. The SAR levels are reduced by more than 60 dB compared to a maximum SAR value at a longitudinal distance of 5 mm from the tip of fourth antenna 1002. The SAR pattern is localized to the region surrounding fourth antenna 1002 and is cut off along first two-wire balanced cable 1000a. The maximum SAR level in the area immediately outside of floating shield 1010 of first two-wire balanced cable 1000a is at least 60 dB below the peak SAR value. This indicates that no electric current flows on an outer surface of floating shield 1010.

As used in this disclosure, the term "mount" includes join, unite, connect, couple, associate, insert, hang, hold, affix, attach, fasten, bind, paste, secure, bolt, screw, rivet, pin, nail, clasp, clamp, cement, fuse, solder, weld, glue, form over, slide together, layer, and other like terms. The phrases "mounted on" and "mounted to" include any interior or exterior portion of the element referenced. These phrases also encompass direct connection (in which the referenced elements are in direct contact) and indirect connection (in which the referenced elements are not in direct contact, but are mounted together via intermediate elements). Elements referenced as mounted to each other herein may further be integrally formed together. As a result, elements described herein as being mounted to each other need not be discrete structural elements. The elements may be mounted permanently, removably, or releasably.

The word "illustrative" is used herein to mean serving as an example, instance, or illustration. Any aspect or design described herein as "illustrative" is not necessarily to be construed as preferred or advantageous over other aspects or designs. Further, for the purposes of this disclosure and unless otherwise specified, "a" or "an" means "one or more". Still further, the use of "and" or "or" is intended to include "and/or" unless specifically indicated otherwise.

The foregoing description of illustrative embodiments of the disclosed subject matter has been presented for purposes of illustration and of description. It is not intended to be exhaustive or to limit the disclosed subject matter to the precise form disclosed, and modifications and variations are possible in light of the above teachings or may be acquired from practice of the disclosed subject matter. The embodiments were chosen and described in order to explain the principles of the disclosed subject matter and as practical applications of the disclosed subject matter to enable one skilled in the art to utilize the disclosed subject matter in various embodiments and with various modifications as suited to the particular use contemplated. It is intended that the scope of the disclosed subject matter be defined by the claims appended hereto and their equivalents.

What is claimed is:

1. An antenna system comprising:
    a coaxial cable comprising
        a center conductor extending a length of the coaxial cable made of a first conductive material;
        a first dielectric material surrounding the center conductor along the length of the coaxial cable; and
        a conductive shield surrounding the first dielectric material along the length of the coaxial cable made of a second conductive material;
    a base fed monopole type antenna comprising a conductor having an electrical length of half a wavelength at a selected operating frequency for the antenna system, wherein the conductor is configured to radiate an electromagnetic wave into surrounding tissue when the antenna system is used; and
    an impedance matching structure comprising
        a second center conductor located between an end of the center conductor of the coaxial cable and a feed connector of the antenna as a continuous extension of the first conductive material of the center conductor of the coaxial cable;
        a second conductive shield that is a continuous extension of the second conductive material of the conductive shield of the coaxial cable;
        a capacitive section located adjacent a feed end of the feed connector of the antenna, the capacitive section comprising
            a second dielectric material surrounding a portion of the second center conductor that extends the length of the capacitive section; and
            a third conductive material that surrounds the second dielectric material along the length of the capacitive section,
            wherein a portion of the second conductive shield that extends the length of the capacitive section surrounds the third conductive material; and
        an inductive section located adjacent the capacitive section on a side of the capacitive section opposite the feed end of the feed connector of the antenna, the inductive section comprising
            a third dielectric material surrounding a portion of the second center conductor that extends the length of the inductive section,
            wherein a portion of the second conductive shield that extends the length of the inductive section surrounds the third dielectric material,
        wherein the impedance matching structure is configured to match an impedance of the coaxial cable to an impedance of the antenna.

2. The antenna system of claim 1, wherein the selected operating frequency is greater than or equal to 300 megahertz and less than or equal to 300 gigahertz.

3. The antenna system of claim 2, wherein the selected operating frequency is greater than or equal to 300 megahertz and less than or equal to 6 gigahertz.

4. The antenna system of claim 1, wherein an insulating material surrounds the conductive shield along the length of the coaxial cable.

5. The antenna system of claim 4, wherein the insulating material further surrounds the second conductive shield along the length of the impedance matching structure.

6. The antenna system of claim 5, wherein the insulating material further surrounds the length of the base fed monopole type antenna.

7. The antenna system of claim 6, wherein a cover extends across an end of the insulating material to enclose the base fed monopole type antenna.

8. The antenna system of claim 7, wherein the insulating material and the cover are moveable relative to the conductor so that, when inserted into the surrounding tissue, the conductor is exposed to the surrounding tissue.

9. The antenna system of claim 1, wherein the feed connector of the antenna extends directly from and in alignment with the second center conductor, wherein the feed connector mounts the conductor to the second center conductor.

10. The antenna system of claim 1, wherein a diameter of the second center conductor is smaller than a diameter of the center conductor of the coaxial cable along the length of the inductive section.

11. The antenna system of claim 10, wherein the diameter of the second center conductor along the length of the inductive section is determined as $$a' = \frac{b}{e^{z'2\pi\sqrt{\frac{\varepsilon}{\mu}}}},$$

where a' is the diameter of the second center conductor, L is an inductance of the inductive section selected to match the impedance, b is an inner diameter of the conductive shield, μ is a permeability of the third dielectric material, and ε is a permittivity of the third dielectric material.

12. The antenna system of claim 1, wherein a dielectric constant of the third dielectric material is less than a dielectric constant of the second dielectric material, and is less than a dielectric constant of the first dielectric material.

13. The antenna system of claim 12, wherein the third dielectric material has a dielectric constant approximately equal to one.

14. The antenna system of claim 12, wherein a length of the third dielectric material along the length of the inductive section is determined as $$\ell = 2\pi L / \mu \ln\left(\frac{b}{a}\right),$$

where L is an inductance of the inductive section selected to match the impedance, μ is a permeability of the third dielectric material, b is an inner diameter of the second conductive shield, and a is a diameter of the second center conductor.

15. The antenna system of claim 1, wherein the inductive section is connected between the capacitive section and the coaxial cable.

16. The antenna system of claim 1, wherein the impedance matching structure further comprises:
a second capacitive section connected between the inductive section and the coaxial cable, wherein the second center conductor extends through the second capacitive section, the second capacitive section comprising
a fourth dielectric material surrounding a portion of the second center conductor that extends the length of the second capacitive section; and
a fourth conductive material that surrounds the fourth dielectric material along the length of the second capacitive section,
wherein a portion of the second conductive shield that extends the length of the second capacitive section surrounds the fourth conductive material.

17. The antenna system of claim 1, wherein the conductive shield and the second conductive shield have a constant outer diameter.

18. The antenna system of claim 1, wherein a length of the capacitive section is determined as $$\ell = C\ln\left(\frac{b}{a}\right) / (2\pi\varepsilon),$$

where C is a capacitance of the capacitive section selected to match the impedance, b is an inner diameter of the third conductive material, and a is a diameter of the second center conductor, and ε is a permittivity of the second dielectric material.

19. The antenna system of claim 1, wherein a dielectric constant of the second dielectric material is greater than a dielectric constant of the first dielectric material.

20. A transmitter comprising:
an antenna system comprising
a coaxial cable comprising
a center conductor extending a length of the coaxial cable made of a first conductive material;
a first dielectric material surrounding the center conductor along the length of the coaxial cable; and
a conductor surrounding the first dielectric material along the length of the coaxial cable made of a second conductive material;
a base fed monopole type antenna comprising a conductor having an electrical length of half a wavelength at a selected operating frequency for the antenna system,
wherein the conductor is configured to radiate an electromagnetic wave into surrounding tissue when the antenna system is used; and
an impedance matching structure comprising
a second center conductor located between an end of the center conductor of the coaxial cable and a feed connector of the antenna as a continuous extension of the first conductive material of the center conductor of the coaxial cable;
a second conductive shield that is a continuous extension of the second conductive material of the conductive shield of the coaxial cable;
a capacitive section located adjacent a feed end of the feed connector of the antenna, the capacitive section comprising
a second dielectric material surrounding a portion of the second center conductor that extends the length of the capacitive section; and
a third conductive material that surrounds the second dielectric material along the length of the capacitive section,
wherein a portion of the second conductive shield that extends the length of the capacitive section surrounds the third conductive material; and
an inductive section located adjacent the capacitive section on a side of the capacitive section opposite the feed end of the feed connector of the antenna, the inductive section comprising
a third dielectric material surrounding a portion of the second center conductor that extends the length of the inductive section,
wherein a portion of the second conductive shield that extends the length of the inductive section surrounds the third dielectric material,
wherein the impedance matching structure is configured to match an impedance of the coaxial cable to an impedance of the antenna;
a signal generator configured to generate a signal at the selected operating frequency; and a connector configured to connect a second end of the coaxial cable opposite the end of the center conductor to the signal generator to receive the generated signal.

* * * * *

UNITED STATES PATENT AND TRADEMARK OFFICE
CERTIFICATE OF CORRECTION

PATENT NO. : 10,765,477 B2
APPLICATION NO. : 14/202786
DATED : September 8, 2020
INVENTOR(S) : Nader Behdad et al.

It is certified that error appears in the above-identified patent and that said Letters Patent is hereby corrected as shown below:

In the Specification

Column 3, Line 53:
Delete the phrase "at a selected operating frequenc" and replace with --at a selected operating frequency--.

Column 6, Lines 15-16:
Delete the phrase "and $\in_1$ is a permittivity of the dielectric material" and replace with --and $\epsilon_1$ is a permittivity of the dielectric material--.

Column 6, Lines 39-40:
Delete the phrase "and $\in_2$ is a permittivity of the dielectric material" and replace with --and $\epsilon_2$ is a permittivity of the dielectric material--.

Column 9, Lines 3-4:
Delete the phrase "and $\in_1$ is the permittivity of polytetrafluoroethylene." and replace with --and $\epsilon_1$ is the permittivity of polytetrafluoroethylene.--.

Column 9, Line 7:
Delete the phrase "and $\in_1$ is the permittivity of Teflon®" and replace with --and $\epsilon_1$ is the permittivity of Teflon®--.

Column 10, Lines 42-43:
Delete the phrase "and E is a permittivity of third dielectric material 602." and replace with --and $\varepsilon$ is a permittivity of third dielectric material 602.--.

Signed and Sealed this
Twenty-ninth Day of December, 2020

Andrei Iancu
*Director of the United States Patent and Trademark Office*

CERTIFICATE OF CORRECTION (continued)
U.S. Pat. No. 10,765,477 B2

In the Claims

Claim 11, Column 15, Lines 15-17:

Delete the phrase " $a' = \dfrac{b}{e^{z'2\pi\sqrt{\frac{\varepsilon}{\mu}}}},$ " and replace with -- $a' = \dfrac{b}{e^{2\pi L\sqrt{\frac{\varepsilon}{\mu}}}},$ --.